(12) United States Patent
Lunin et al.

(10) Patent No.: US 12,202,875 B2
(45) Date of Patent: Jan. 21, 2025

(54) GBD-SSTAD-SSTAD RECOMBINANT PROTEIN AND METHOD FOR PRODUCING AND USING SAME

(71) Applicant: Limited Liability Company "URSPHARM", Moscow (RU)

(72) Inventors: Vladimir Glebovich Lunin, Moscow (RU); Sergei Mihailovich Yudin, Moscow (RU); Vyacheslav Viktorovich Rechetnik, Moscow (RU); Vali-Magomed Kadievich Magataev, Moscow (RU)

(73) Assignee: LIMITED LIABILITY COMPANY "URSPHARM", Moscow (RU)

( * ) Notice: Subject to any disclaimer, the term of this patent is extended or adjusted under 35 U.S.C. 154(b) by 721 days.

(21) Appl. No.: 17/435,358

(22) PCT Filed: Dec. 2, 2020

(86) PCT No.: PCT/EA2020/000003
§ 371 (c)(1),
(2) Date: Aug. 31, 2021

(87) PCT Pub. No.: WO2021/129915
PCT Pub. Date: Jul. 1, 2021

(65) Prior Publication Data
US 2022/0235112 A1 Jul. 28, 2022

(30) Foreign Application Priority Data
Dec. 25, 2019 (RU) .................................. 2019143669

(51) Int. Cl.
*C07K 14/655* (2006.01)
*A61K 9/00* (2006.01)
*A61K 39/00* (2006.01)
*C07K 7/64* (2006.01)
*C07K 14/315* (2006.01)

(52) U.S. Cl.
CPC .......... *C07K 14/655* (2013.01); *A61K 9/0019* (2013.01); *C07K 7/64* (2013.01); *C07K 14/315* (2013.01); *A61K 39/00* (2013.01)

(58) Field of Classification Search
None
See application file for complete search history.

(56) References Cited

U.S. PATENT DOCUMENTS

| 4,261,885 A | 4/1981 | Sakakibara et al. |
| 6,316,004 B1 | 11/2001 | Lunin et al. |
| 7,888,030 B2 | 2/2011 | Butt et al. |
| 2007/0155659 A1 | 7/2007 | Gougeon |

FOREIGN PATENT DOCUMENTS

| EP | 1522311 A1 | 4/2005 |
| EP | 2835136 A1 | 2/2015 |
| EP | 2291194 B1 | 2/2017 |
| RU | 2031121 C1 | 3/1995 |
| RU | 2337708 C1 | 11/2008 |
| RU | 2493873 C1 | 9/2013 |
| RU | 2526571 C1 | 8/2014 |
| RU | 2561467 C1 | 8/2015 |

OTHER PUBLICATIONS

D.K. Novikov, "Medical Immunology," Ministry of Health of The Republic of Belarus, Vitebsk State Medical University, 2002, 235 pages.
Poletaev et al., "Immunophysiology versus immunopathology: Natural autoimmunity in human health and disease," Pathophysiology vol. 19 (2012) pp. 221-231, 11 pages.
Andreani et al., "Somatostatin action on rat ovarian steroidogenesis," Human Reproduction vol. 10, No. 8 (1995) pp. 1968-1973, 6 pages.
Ashmarin et al., "Immunizing Albino Rats With a Covalent Sydnophen-Serum Albumin Conjugate Depresses Chronic Ethanol Consumption," Department of Human and Animal Physiology, M. V. Lomonosov Moscow University, Translated from Byulleten Eksperimental'noi Biologii i Meditsiny, vol. 108, No. 12, pp. 695-697, Dec. 1989, 4 pages.
Alexander Poletaev, "Physiologic Autoimmunity and Preventive Medicine," Medical Research Center "Immunculus", Moscow, Russia, 2013, 37 pages.
Cora et al., "Vaginal Cytology of the Laboratory Rat and Mouse:Review and Criteria for the Staging of the Estrous Cycle Using Stained Vaginal Smears," Toxicologic Pathology, 43: 776-793, 2015, 18 pages.
Dubreuil et al., "Long-term Growth Hormone-Releasing Factor Administration on Growth Hormone, Insulin-like Growth Factor-I Concentrations, and Bone Healing in the Beagle," Can J Vet Res 1996; vol. 60: pp. 7-13, 7 pages.
Dixon et al., "Nonproliferative and Proliferative Lesions of the Rat and Mouse Female Reproductive System," J Toxicol Pathol 2014; 27 (3&4 Suppl): pp. 1S-107S, 107 pages.

(Continued)

*Primary Examiner* — Brian Gangle
(74) *Attorney, Agent, or Firm* — Muncy, Geissler, Olds & Lowe, P.C.

(57) ABSTRACT

The present invention relates to genetic engineering, biotechnology, immunology, and microbiology. Recombinant GBD-SSTad-SSTad protein and a method for preparation thereof on glucan are described, including the binding of GBD-SSTad-SSTad protein in cell extracts of *E. coli* BL21 [pGBD-SSTad-SSTad] strain to an alpha-glycan-containing sorbent due to affinity interaction during the incubation procedure, subsequent washing from unbound bacterial proteins and isolation of the desired product. The invention also relates to an immunogenic composition and a kit comprising said peptide. The invention also relates to the use of the obtained protein to increase the number of maturing follicles and improve the quality of sperm. This technical result, an increase in the number of maturing follicles and an improvement in the quality of sperm is based on the use of the KNFFWKTFTS peptide, which is part of a recombinant protein that is capable of eliciting autoantibodies to somatostatin.

6 Claims, 1 Drawing Sheet
Specification includes a Sequence Listing.

(56) References Cited

OTHER PUBLICATIONS

A. Gougeon, "Regulation of resting follicle activation," Gynécologie Obstétrique & Fertilité vol. 39 (2011) pp. 511-513, 3 pages.

Gougeon et al., "Kit Ligand and the Somatostatin Receptor Antagonist, BIM-23627, Stimulate in Vitro Resting Follicle Growth in the Neonatal Mouse Ovary," Endocrinology, Mar. 2010, 151(3): pp. 1299-1309, 11 pages.

Heidarpour et al., "Effects of somatostatin analog treatment on cardiovascular parameters in patients with acromegaly: A systematic review," Journal of Research in Medical Sciences, 2019, pp. 1-10, 10 pages.

Holst et al., "Somatostatin in human follicular fluid," Human Reproduction vol. 9 No.8 (1994), pp. 1448-1451, 4 pages.

Huang et al., "The Murine Steel Panda Mutation Affects Kit Ligand Expression and Growth of Early Ovarian Follicles," Developmental Biology vol. 157, pp. 100-109 (1993), 10 pages.

Ingrid Böhm, "Disruption of the Cytoskeleton After Apoptosis Induction with Autoantibodies," Autoimmunity, 2003 Vol. 36 (3), pp. 183-189, 8 pages.

Itakura et al., "Expression in Escherichia coli of a Chemically Synthesized Gene for the Hormone Somatostatin," Science, vol. 198, 1977, pp. 1056-1063, 8 pages.

"WHO laboratory manual for the Examination and processing of human semen, Fifth Edition," World Health Organization, 2010, 286 pages.

Lamberts et al., "The Role of Somatostatin and Its Analogs in the Diagnosis and Treatment of Tumors," Endocrine Reviews vol. 12, No. 4 (1991), pp. 450-482, 33 pages.

Lidor et al., "Combined somatostatin analog and follicle-stimulating hormone for women with polycystic ovary syndrome resistant to conventional treatment," Gynecol Endocrinol 1998; 12:97-101, 5 pages.

Macleod et al., "The Male Factor in Fertility and Infertility," Sperm Morphology vol. 2, No. 5 (1951) pp. 394-414, 21 pages.

Lin et al., "Evolution of neuroendocrine peptide systems: Gonadotropin-releasing hormone and somatostatin," Comparative Biochemistry and Physiology Part C 119 (1998) pp. 375-388, 14 pages.

Macomber et al., "The Spermatozoa Count, Its Value In The Diagnosis, Prognosis and Treatment of Sterility," The New England Journal of Medicine vol. 200 No. 19 (1929) pp. 981-984, 4 pages.

Maicas et al., "Construction of an Expression Vector for Production and Purification of Human Somatostatin in *Escherichia coli*," Mol Biotechnol (2013), 9 pages.

Nespovitaya et al., "The production of recombinant 15N, 13C-labelled somatostatin 14 for NMR spectroscopy," Protein Expression and Purification (2014) pp. 1-9, 9 pages.

Milosevic et al., "Centrally Applied Somatostatin Influences Morphology of Pituitary FSH Cells But Not FSH Release," Gen. Physiol. Biophys. (2004), vol. 23, pp. 375-380, 6 pages.

McNeill et al., "Neuropeptides in Sensory Perikarya Projecting to the Rat Ovary," The American Journal of Anatomy vol. 179: pp. 269-276 (1987), 8 pages.

Mori et al., "Evidence for existence of somatostatin-like immunoreactivity with molecular heterogeneity in porcine ovaries," Acta Endocrinologica 1984, vol. 106, pp. 254-259, 6 pages.

Parrott et al., "Kit-Ligand/Stem Cell Factor Induces Primordial Follicle Development and Initiates Folliculogenesis," Endocrinology vol. 140, No. 9, pp. 4262-4271, 10 pages.

Rajkumar et al., "Inhibitory action of somatostatin-14 on hormone-stimulated cyclic adenosine monophosphate induction in porcine granulosa and luteal cells," Journal of Endocrinology (1992) vol. 134, pp. 297-306, 10 pages.

Reubi et al., "Somatostatin Receptors in Human Endocrine Tumors," Cancer Research vol. 47 (1987) pp. 551-558, 9 pages.

Reisine et al., "Molecular Biology of Somatostatin Receptors," Endocrine Reviews vol. 16, No. 4 (1995) pp. 427-442, 16 pages.

Spencer et al., "The Effect of Immunization Against Somatostatin On Growth Rates and Growth Hormone Secretion in the Chicken," Camp. Biochem. Physiol. vol. 85A, No. 3 (1986) pp. 553-556, 4 pages.

G S G Spencer,"New approach to regulation of growth using immunization against somatostatin: discussion paper," Journal of the Royal Society of Medicine vol. 77 Jun. 1984, pp. 496-500, 5 pages.

Westbrook et al., "Active immunization against somatostatin alters regulation of gastrin in response to gastric acid secretagogues," American Journal of Physiology (1998), pp. G751-G756, 6 pages.

Sadeu et al., "Folliculogenesis and oogenesis in vivo and in vitro, in humans females," Physiologie, pathologie et thérapie de la reproduction chez l'humain (2011), 2 pages.

Ting et al., "Treatment of female rhesus macaques with a somatostatin receptor antagonist that increases oocyte fertilization rates without affecting post-fertilization development outcomes," Journal of Assisted Reproduction and Genetics (2019) vol. 36: pp. 229-239, 11 pages.

Ala-Gly-Cys-Lys-Asn-Phe-Phe-Trp
|                              |
Cys-Ser-Thr-Phe-Thr-Lys

GBD-SSTAD-SSTAD RECOMBINANT PROTEIN AND METHOD FOR PRODUCING AND USING SAME

CROSS-REFERENCE TO RELATED APPLICATIONS

This application is a National Stage of International Application No. PCT/EA2020/000003 filed on Dec. 2, 2020, which claims priority of Application No. 2019143669 filed in Russia on Dec. 25, 2019 under 35 U.S.C. § 119, the entire contents of all of which are hereby incorporated by reference.

REFERENCE TO SEQUENCE LISTING SUBMITTED VIA EFS-WEB

This includes an electronically submitted sequence listing in .txt format. The .txt file contains a sequence listing entitled "6626 0109PUS1 ST25.txt" created on Mar. 6, 2022 and is 12,969 bytes in size. The sequence listing contained in this .txt file is part of the specification and is hereby incorporated by reference herein in its entirety.

DESCRIPTION

Field of the Invention

The present invention relates to genetic engineering, biotechnology, immunology, and microbiology. Specifically, the invention relates to a recombinant protein GBD-SSTad-SSTad and a method for production thereof on glucan, comprising the binding of the protein GBD-SSTad-SSTad in cell extracts of *E. coli* BL21 [pGBD-SSTad-SSTad] strain with an alpha-glycan-containing sorbent due to an affinity interactions during the incubation procedure, subsequent washing from unbound bacterial proteins and isolation of the desired product. The invention also relates to an immunogenic composition and a kit comprising said peptide. The invention also relates to the use of the obtained protein to increase the number of maturing follicles and improve the quality of sperm. This technical result of increasing the number of maturing follicles and improving the quality of sperm is based on the use of the KNFFWKTFTS (SEQ ID NO: 1) peptide, which is part of a recombinant protein capable of inducing autoantibodies to somatostatin. Therefore, the invention can be used to treat male and female infertility.

Background of the Invention

In humans, folliculogenesis begins when some resting follicles leave the ovarian reserve to enter the growing phase. The activation of resting follicles remains a poorly studied process; however, modern literature data indicates the existence of a spectrum of interrelated factors, which regulate the dynamics of the balance of numerous factors of activation and suppression of follicular development. The regulation of molecular mechanisms, responsible for controlling the activation of resting follicles may have significant clinical applications for the process of mobilizing resting follicles in patients suffering from infertility due to ovarian dysfunction. Recently, somatostatin, which has a systemic inhibitory effect on the hypothalamic-pituitary-ovarian system, is of increasing interest to specialists (Gougeon et al., 2010, Endocrinology. 151 (3): 1299-309).

The mechanisms regulating the initiation of follicular growth remain poorly understood. Kit ligand (KL) is the first protein discovered that triggers follicular growth. This is based on the analysis of the phenotype of the ovary in animals carrying spontaneous inactivating KL mutations (Huang et al., 1993, Dev. Biol, 157: 100-109) and experimental studies (Yoshida et al., 1997, Dev. Biol. 184: 122-137; Parrott et al., 1999; Endocrinology 140: 4262-4271). The opposite, inhibitory effect on the initiation of follicular growth is caused by the peptide hormone somatostatin (SST). SST has a strong inhibitory effect on a number of hormones (somatotropin, thyroid-stimulating hormone, insulin, glucagon, gastrin, pepsin), initiates inhibition of the secretion of enzymes of the stomach, pancreas, and small intestine, slowing down the motility of the gastrointestinal tract and the evacuation of its contents. There is evidence that the hypothalamic-pituitary-ovarian system is also a target for SST (Gougeon et al., 2010, Endocrinology 151 (3): 1299-309).

SST is a cyclic U-shaped peptide present in two forms in the body (SST-14 comprising 14 amino acids and SST-28 comprising 28 amino acids). The biological activities of these two forms of SST are identical. The SST-14 form is predominant in the central nervous system, inhibiting the secretion of growth hormone by somatotropic cells of the anterior pituitary gland. The SST-28 form is predominantly present in the stomach and pancreas. The biological activity of SST is mediated by several membrane receptors in combination with protein G, 5 subtypes of which have been characterized, namely the SSTR1-SSTR5 subtypes (Reubi, 1987, Cancer Res. 47: 551-558; Resine et al., 1995, Endocrin Reviews 16: 427-442; Lamberts et al., 1991, Endocrin Reviews 12: 450-482).

The presence of SST in the ovary has been reported for several mammalian species, including pigs (Mori et al., 1984, Acta Endocrinol. (Copenh.) 106 (2): 254-259), rats (McNeill et al., 1987, Am. J Anat. 179 (3): 269-76) and humans (Hoist et al, 1994, Hum. Reprod. 9 (8): 1448-1451). SST receptors have been identified in rat ovaries (Lidor et al., 1998, Gynecol. Endocrinol. 12 (2): 97-101) as well as in the human ovary, in particular subtypes 1, 2A and 5 (Strauss et al., 2003, Hum Reprod 18 (1): 495-507). Therefore, there is reason to conclude that the ovaries of all mammalian species contain SST and its receptors. Another data provided in the previous patents allows to propose the presence of SST and its receptors in the ovaries of birds (RU 2337708, RU 2526571, Kudryavets N. I., 2018, Gorki BGSKhA, Biological characteristics of birds of different species).

Experimental evidence suggests that SST may play a role in keeping follicles at resting state. SST is a peptide with a well-known effect in endocrine tissues: it inhibits the formation of cAMP (Ben-Shlomo et al., 2007, I Drugs. 10 (12): 885-95), and also inhibits the production of KL by Sertoli cells (similar to granulosa cells) in the testis of male pigs. In rats, when SST is administered in vivo, the number of preovulatory ovarian follicles decreases (Nestorovic et al., 2004, Gen Physiol Biophvs. 23 (3): 375-80), and in vitro SST inhibits the production of FSH-stimulated aromatase and progesterone by granulosa cells (Andreani et al., 1995, Hum Reprod. 10 (8): 1968-73). In porcine ovarian granule cells, SST inhibits luteinizing hormone (LH) and forskolin-stimulated cAMP production (Rajkumar et al., 1992 J Endocrinol. 134 (2): 297-306) and may inhibit nuclear maturation of perivascular oocytes.

SST also plays a key role in controlling the proliferation of male germ cells. SST receptors (SSTRs) SSTR3, SSTR4 and SSTR5 are abundantly expressed in normal human testicular tissue, while SSTR1 and SSTR2 are generally absent. In rat testes, SSTR1, SSTR2, and SSTR3 receptors have been identified mainly in spermatocytes. In addition, intense accumulation of SSTR1-3 mRNA is observed in round spermatids at stages I-VII of formation and decreases drastically at stage IX, when round spermatids are already beginning to change. All the above-mentioned facts indicate the direct involvement of SST and its receptors in mammalian spermatogenesis. Prior patents data suggests the participation of SST and its receptors in the spermatogenesis of birds (RU 2337708, RU 2526571, Kudryavets N. I., 2018, Gorki BGSKhA, Biological characteristics of birds of different species).

The above-mentioned facts strongly suggest that SST is one of the factors maintaining the follicle and spermatid resting stages. By inhibiting the production of cAMP in granulosa cells, SST can limit the production of KL. Therefore, SSTR antagonists or antibodies that bind and neutralize SST activity can stimulate the transition of follicles and spermatids during the growth phase.

The first of the above-mentioned approaches was used in a number of researches and patents by A. Gougeon et al. (Gougeon, 2011, Gynecol Obstet Fertil. 39 (9): 511-3; Gougeon et al., 2010, Endocrinology 151 (3): 1299-309; Gougeon and Loumaye, EP 20040791488 08.10.2004; Gougeon, US 20070155659 A1 5.7.2007; Tranand and Gotteland, EP 2835136 A1 11.02.2015), which described the use of an SST antagonist analog for the preparation of a medicament intended to accelerate the onset of growth of resting follicles. The authors have developed SST antagonist analogs, which are cyclic or non-cyclic polypeptides having high affinity for the SST receptor and inhibiting the functional activity of SST14 or SST28, such as inhibition of growth hormone secretion by pituitary somatotropic cells and/or in vitro inhibition of pituitary adenoma cell proliferation. Most SST antagonist analogs had high affinity for all or at least 2 or 3 SST receptor subtypes, or greater affinity for at least one of subtypes 1, 2, 3, 4, and 5 (for example, subtype 2). Under the term "SST agonist analog" in the published patents the compound for which an effective dose of DE50 is 1 µM or less for at least one of the somatostatin receptor subtypes, is described. In the neonatal murine ovary, the SST receptor antagonist decreased in the percentage of primordial follicles and an increase in the percentage of primary and secondary follicles (Gougeon et al., 2010, Endocrinology. 151 (3): 1299-309).

Gougeon US 20070155659 A1 5.7.2007 found that SST and its analogs are able to impact the transition of follicles from the resting stage to the growth stage. The author has demonstrated the use of SST or an SST agonist analog for the preparation of a drug intended to reduce or inhibit the onset of growth of resting follicles. On the contrary, the use of SST antagonist analog accelerated the onset of growth of resting follicles. Therefore, it was demonstrated for the first time that, by using modified SST derivatives, it was possible to directly affect the growth of follicles, accelerating or slowing down their development. For each mouse, one ovary was incubated in culture medium (control) and the other ovary was incubated in the presence of SST or KL or the SST antagonist BIM-23627. After that, the ovaries were histologically evaluated for the content of primordial, primary and secondary follicles. It was shown that KL and BIM-23627 caused a decrease in the percentage of primordial follicles and increased the percentage of primary and secondary follicles compared with those in control mice ovaries.

The inventors intend to use SST antagonist analogs for in vitro or in vivo fertilization of animals having a high market value. Such animals, in particular, may include horses, ruminants, sheep or goats; they may also include transgenic animals. The inventors find the main advantage of the developed technique in preparing a drug based on SST antagonist analog, in order to activate the resting follicles of the ovarian reserve of animals and initiate the growth phase. Administration of such a drug to animals for 1-12 months increases the number of follicles in the growth phase that can be stimulated by standard treatment options to reach the preovulatory follicle stage. Similar data were obtained in Tran and Gotteland patent EP 2835136 A1 11.02.2015.

Similar results were observed in rhesus monkeys after the use of the SST antagonist PGL1001 (Ting et al., 2019, J Assist. Reprod. Genet. 36 (2): 229-239). Systemic administration of PGL1001 did not affect the overall health of the animals, the duration of the menstrual cycle, or the levels of circulating ovarian hormones compared to the control group. Treatment with PGL1001 increased the ovarian circumference, as well as the rate of fertilization of oocytes, compared with the same parameters in the control group of animals receiving placebo.

However, the proposed technique has a number of limitations in its use, since it requires the systematic use of expensive derivatives of SST antagonists over many months. It is possible to reduce the concentration of SST in the blood of animals and to reduce binding to the receptors of the hypothalamic-pituitary-ovarian system not only by using antagonist analogs, but also by the technique of neutralization of SST activity by autoantibodies.

The immune system of the body, in addition to the protective function, carries out regulatory functions in relation to cell proliferation and other genetically determined functions of its own cells, by creating specific autoantibodies to biologically active compounds of the body (Poletaev A. B. et al., 2002, Medicine: 168-172). Autoantigens, in contrast to antigens, are self-proteins, protein complexes or components of body cells that become partially allogenic under the influence of various damaging factors and infectious agents or because of a deliberate violation of natural immunological tolerance, which, in this case, is achieved by the administration of a specially formulated endogenous antigen. The production of these antibodies can be induced by inverse immunoregulation. The method of inverse immunoregulation is based on the induction of autoantibodies to endogenous biologically active compounds by introducing the latter in the form of covalent conjugates with carrier antigens, as a result of which physiological functions in the body are permanently and purposefully changed. The term was proposed by I. P. Ashmarin (Ashmarin et al., 1989, Bull Exp Biol Med 12: 695-697). In the foreign literature, the term autoantigenicity is used to describe the mentioned condition (Poletaev et al., 2012, Pathophysiology 19 (3): 221-31).

Antibodies to endogenous biologically active compounds, in particular hormones, can bind and reduce the concentration as well as the biological activity of the corresponding compounds (Bohm, 2003, Autoimmunity 36: 183-189). This results in smooth changes in a number of physiological and biochemical processes, with which the hormonal regulator is directly or indirectly associated. In this case, the molecule containing the entire SST or any fragment of the SST acts as an immunogen (an autoantigen that induces an immune response) that causes the body to produce antibodies against this endogenous factor. These antibodies will bind endogenous SST, so they will become autoantibodies, which reduce its concentration in the blood, and, accordingly, prevent interaction with specific receptors and weaken its physiological effect on the body.

More than thirty years ago, in the USA, Canada, Great Britain and Russia independent research groups carried out the experiments on active immunization of animals (cattle, sheep, pigs) to somatostatin-14 (Spencer, 1984, J R Soc Med. 77 (6): 496-500). The study author c notes that in terms of the dynamics of an increase in body weight, the immunized animals exceeded the control individuals by 15-20% in the same conditions of maintenance, whereupon an increased content of endogenous somatotropic hormone was found in the blood. Subsequently, experiments were carried out with different types of animals. Active immunization of animals with proteins obtained from the covalent conjugation of synthetic SST to carrier proteins resulted in increased levels of growth hormone (Spencer et al., 1986, Comp Biochem Physiol A Comp Physiol. 85 (3): 553-6), insulin growth factor (Dubreuil et al., 1991, Domest Anim Endocrinol. 8 (2): 307-21), gastrin (Westbrook et al., 1998, Am J Physiol. 274 (4): 751-6) and other biologically active compounds associated with somatostatin. The result of active antisomatostatin immunization was an increase in the body weight of animals by 8-17%.

The method of somatostatin immunoneutralization is devoid of many of the disadvantages that rise from utilizing the anabolic hormones or recombinant somatotropin. Mechanism of action of somatostatin immunoneutralization is based on the temporary binding of endogenous SST by specific antibodies and an increase in the concentration of endogenous growth hormone in the body of an animal within physiological limits. However, the widespread use of the method of active immunization of animals against endogenous SST-14 for a long time was impossible due to its high cost, since the main way for producing the peptide was chemical synthesis, which economically limited the implementation of this approach in practice. The small size of SST-14 does not allow its direct microbial synthesis using recombinant DNA technology, several methods of its synthesis in the form of chimeric proteins have been described, followed by the isolation of the desired product, which did not provide satisfactory results (Itakura et al., 1977, Science 198 (4321): 1056-63; Nespovitaya et al., 2014, Protein Expr Purif 99: 78-86; Maicas et al., 2013, Mol Biotechnol. 55 (2): 150-158).

Lunin V. G. et al. patent RU 2031121 CT developed an injectable preparation for increasing meat and dairy productivity of farm animals and poultry based on a chimeric protein comprising water-insoluble enzymatically inactive chloramphenicol acetyltransferase (Sat) without 10 C-terminal amino acids, an amino acid spacer, and SST-14 having amino acid sequence AGCKNFFWKTFTSC (SEQ ID NO: 11) (Som) in oil solution with additives.

Lunin V. G. et al. have been granted the patent RU 2561467 for "A method of production of preparation to increase meat and milk productivity of farm animals (options) and preparation produced by method." Yudin S. M. et al. found that the previously developed preparation Sat-Som based on recombinant SST also improved reproductive abilities, helping to increase the sperm production of male farm animals, roosters and humans (patent application RU(11) 2493873(13) Cl Yudin S. M. et al. "Injectable preparation for increasing sperm production in stud livestock and roosters and method for use thereof"; Russian Federation patent for invention No. 2526571, Yudin S. M. and Yudina T. I." Injectable preparation for increasing human sperm production and method for use thereof"). Both inventions are intended to increase the reproductive abilities of the body, increase the volume of ejaculate and improve some of the quality parameters of sperm. The injectable preparation was used in males, farm animals and humans at the stage of physiological maturity at a dose of 50-200 µs of chimeric Sat-Som protein per 1 kg of live weight. The inventions allow to improve sperm production: to increase the volume of ejaculate and to reduce the waste of sperm in terms of biological indicators in stud livestock, roosters and humans by using the injectable preparation. Following studies carried out by the applicants showed that immunization with somatostatin-containing Sat-Som drug in female rats led to an increase in the size of the ovary, as well as in an increase in size of primary and secondary follicles in the ovary of animals (Yudin S. M. et al., 2017; Effect of somatostatin-containing preparation on folliculogenesis. Issues of gynecology, obstetrics and perinatology. 16 (2): 26-33).

However, the technique of purification of discussed somatostatin-containing protein Sat-Som does not result in a complete removal of some bacterial proteins, lipopolysaccharides and DNA of the producer strain, which does not correspond to modern quality biotechnological standards for the immunobiological preparations. The formation of the correct native U-shaped structure of SST along with the formation of the cysteine bridge between cysteines in the third and fourteenth positions is also a challenging task (FIG. 1).

To overcome this technological limitations, a new somatostatin containing recombinant protein has been developed, which consists of glucan binding domain (GBD), separating spacer (sp) and two truncated SST variants with the sequence KNFFWKTFTS (SEQ ID NO: 1), which has been called the antigenic determinant of somatostatin (SSTad): GBD-sp-SSTad-sp-SSTad.

The peptide having the sequence KNFFWKTFTS (SEQ ID NO: 1) is refered in the U.S. Pat. No. 4,261,885. However, this document refers to the suppression of the proliferation of pituitary adenoma cells. Therefore, the expert could not find the distinct connection between the specified peptide and the purpose for which the present invention is used, and the technical result achieved by the implementation of the invention. It was mentioned above that the small size of somatostatin-14 becomes a challenging problem within microbial synthesis, which has not allowed the authors to look for ways to develop it's synthesis methods, associated with an even greater decrease in the size of the peptide. It should be assumed that it is the somatostatin fragment of the indicated 10 amino acids that will show itself as an effective means for increasing folliculogenesis and spermatogenesis in mammals, birds and humans.

Unlike the approach developed by Geugeon et al., which requires the systemic use of expensive SST antagonist analog derivates for many months, the technique of the proposed invention allows to reduce the concentration of SST in the blood of animals and reduce the binding of SST to receptors after two or three immunizations with a preparation of recombinant somatostatin-containing protein, allowing to reach the optimal titer of autoantibodies for neutralization.

The aim of the present invention is to develop a method for stimulation of folliculogenesis and spermatogenesis in humans, mammals, animals and birds with immunogenic somatostatin-containing composition via binding endogenous SST, increasing the activity of sex hormones in blood serum and inducing complex rearrangements in the form of adaptive genesis, which are manifested in structural transformations of reproductive system organs aiming for the stimulation of the reproductive potential of mammals, birds and humans, by means of using an injectable preparation that meets the requirements for the analysis of pharmaceutical substances using approved adjuvants, which allows to administer injections without adverse painful sensations.

Based on this goal, the object of the present invention is to develop a recombinant immunologically active somatostatin-containing protein that is easily purified and has sufficient immunogenicity against SST as an antigen, which can be used to stimulate folliculogenesis and spermatogenesis in mammals, birds and humans, due to induction of the synthesis of specific autoantibodies to SST blocking its activity. Another object of the invention is to formulate a preparation based on said protein and to develop a method for use of that preparation, which solves the problem of obtaining autoantibodies to SST in the body, leading to an increase in the concentration of sex hormones and in the activity of folliculogenesis and spermatogenesis in mammals, birds and humans after the systemic administration of the preparation. It should be noted that the amino acid sequence of SST is identical in both humans and all mammals and birds. As a result, the developed preparation is a universal remedy for enhancing folliculogenesis and spermatogenesis in humans, mammals and birds.

The advantage of the above-mentioned solution is due to the possibility of preparing a medication, which is based on the SST autoantigen to accelerate the onset of growth of resting follicles. On average, of six married couples planning to have a child one has difficulty in conceiving. Although there are many reasons for the polyetiology of this ailment, two treatment options have been developed and are commonly used to treat human infertility, called "medically assisted childbirth", which aim to introduce the simultaneous growth of multiple preovulatory follicles. This allows to obtain several mature oocytes and thus several embryos, leading to increase in the chance for conception. This is achieved by administering one or more drugs that stimulate the secretion of gonadotropins FSH (follicle stimulating hormone) and LH by the pituitary gland, such as an antiestrogen (for example, clomiphene citrate or tamoxifen) or an aromatase inhibitor (for example, letrozole, anastrazole or exemestane). Simultaneous growth of several preovulatory follicles can also be induced by administering a human FSH preparation (extractive or recombinant) with or without LH. When the follicles reach the preovulatory size, depending on the cause of sterility, one of two treatment options (type of therapy) is selected. The first is intrauterine fertilization (IUI), and the second is the removal of oocytes from the ovary by aspiration of follicles (5 to 15 oocytes) and fertilization in the laboratory (in vitro), either by simple co-incubation of oocytes with the partner's sperm (IVF), or microinjection of sperm directly into the oocyte (ICSI). It is imperative to obtain several mature oocytes in order to optimize the success rate (pregnancy rate) with this treatment; however, in some women, despite adequate ovarian stimulation, the number of oocytes obtained is low or even equal to one. The poor response to stimulant treatment is the result of the limited number of growing follicles that are present in the ovaries of these patients. Therefore, the ability to activate the ovarian reserve follicles and force them to enter the growth phase is a significant therapeutic benefit. The advantage of this solution lies primarily in the possibility of using the SST autoantigen in the treatment of female infertility.

Another object of the present invention is the use of the SST autoantigen for the preparation of a drug to accelerate the onset of growth of resting follicles in non-menopausal females and spermatocytes in males. The administration of such a drug increases the number of follicles in the growth phase in females, which can be stimulated with standard treatments to reach the stage of preovulatory follicles, and also sperm count rates in males. At the beginning of the 20th century, the concentration of 60-100 million spermatozoa in 1 ml of ejaculate passed for normal (Macomber and Sanders, 1929, N Engl J. Med. 200: 981), while the lower limit of the sperm concentration in the ejaculate, conventionally separating normospermia from oligozoospermia, was later reduced, at first to 40 million/ml, then to 20 million/ml (Mac Leod and Gold, 1951, J. Urol. 66: 436-442). In accordance with the latest WHO recommendations in 2010, the concentration of 15 million spermatozoa in 1 milliliter of ejaculate is considered as the normal rate. The decrease in the activity of spermatogenesis continuing for unclear reasons urgently requires its stimulation not only in pathologies, but also in normal condition, according to the WHO 2010 criteria, germ cell production (World Health Organization. Laboratory Manual for the Examination of Human Semen and Sperm-Cervical Mucus Interaction. Cambridge: Cambridge Univ. Press, 2010).

According to the present invention, the pharmaceutical preparation, containing the SST antigenic determinant, can be administered by the parenteral route (subcutaneously, intramuscularly, intraperitoneally, intravenously) or by the transdermal route. The subcutaneous route is preferred because it allows effective concentrations of the active ingredient to be delivered to dendritic cells and macrophages. From the SST antigenic determinant used in the composition of a recombinant protein with permitted adjuvants and necessary excipients, a dosage form is prepared to make it possible to administer efficiently and reproducibly for each route of administration.

The dose of the preparation of the present invention for the treatment of the above-mentioned diseases or disorders and the number of vaccinations may vary depending on the route of administration, the age and body weight of the patient, as well as the condition of the patient. The final decision on therapy regimen is made by physician or veterinarian, respectively.

According to the results of the present invention, the applicants have found that it is possible to suppress SST receptor responses by inducing the synthesis of specific autoantibodies to the SST antigenic determinant. This leads to a pharmacological effect on the ovarian reserve, which is an acceleration of the onset of growth of resting follicles causing a decrease in the percentage of primordial follicles and an increase in the percentage of primary and secondary follicles in comparison with similar parameters in control groups of animals, as well as an increase in spermatogenesis in mammals, birds and humans.

SUMMARY OF THE INVENTION

The present invention provides with the new use of the peptide antigenic determinant of somatostatin KNFFWKTFTS (SEQ ID NO: 1) and its analogs as part of fusion recombinant proteins that are capable to accelerate folliculogenesis and spermatogenesis in mammals, birds and humans.

In a first aspect, the invention relates to recombinant GBD-SSTad-SSTad protein having a molecular weight of 39.5 kDa, which comprises 2 fragments of the SST protein having the sequence SEQ ID NO 1, Gly-Ser spacer having the sequence SEQ ID NO 2 or the sequence SEQ ID NO 3, the alpha-glucan binding domain of a gene from *Streptococcus mutans* having the sequence SEQ ID NO 4, the recombinant protein (SEQ ID NO: 6) is encoded by the nucleotide sequence of the GBD-SSTad-SSTad gene SEQ ID NO 5.

In a second aspect, the invention relates to a method for producing recombinant GBD-SSTad-SSTad protein on glucan, which includes: binding the GBD-SSTad-SSTad protein in cell extracts of *E. coli* BL21 [pGBD-SSTad-SSTad] strain to an alpha-glycan-containing sorbent due to affinity interaction during the incubation procedure, subsequent washing from unbound bacterial proteins and isolation of the desired product.

In a third aspect, the invention relates to a pharmaceutical composition, which is an injectable preparation for enhancing folliculogenesis and spermatogenesis in mammals, birds and humans, comprising recombinant GBD-SSTad-SSTad protein and an adjuvant suitable for injection.

In a fourth aspect, the invention provides a method for enhancing folliculogenesis and spermatogenesis in mammals, birds and humans, by means of subcutaneous or intramuscular injections of a preparation containing recombinant GBD-SSTad-SSTad protein at a dose of 5-200 µg of said protein per kilogram of body weight of a mammal or bird.

In addition, the invention may relate to a pharmaceutical package or kit comprising one or more containers filled with the recombinant protein according to the invention containing the antigenic determinant of somatostatin KNFFWKTFTS (SEQ ID NO: 1) as part of recombinant fusion proteins.

DETAILED DESCRIPTION OF THE INVENTION

Figures 1, 2:
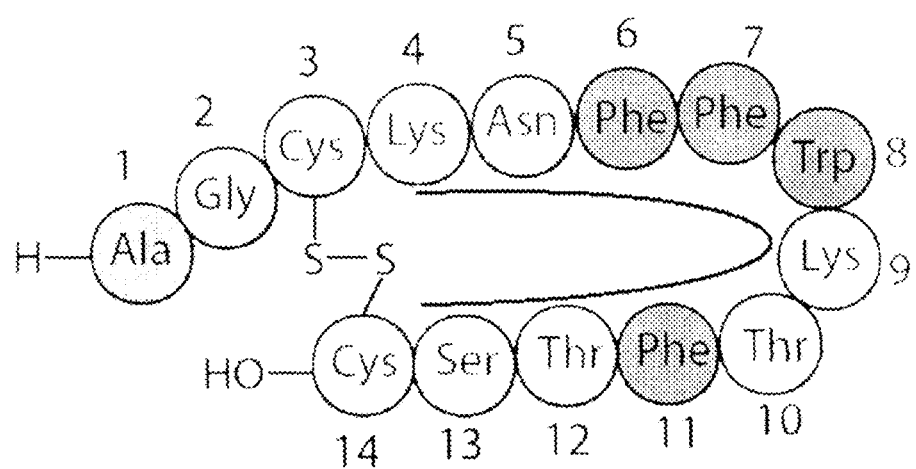
FIG. 1 (SEQ ID NO: 11) is an illustration of a U-shaped structure along with the formation of a cysteine bridge between cysteines in the third and fourteenth positions that is crucial for peptide conformation and bioactivity.
FIG. 2 (SEQ ID NO: 11) is an illustration of a U-shaped structure of somatostatin positions that is crucial for peptide conformation and bioactivity.

The present invention relates to a compound, comprising the antigenic determinant of somatostatin KNFFWKTFTS (SEQ ID NO: 1) as part of fusion recombinant proteins to accelerate the onset of growth of resting follicles, folliculogenesis and spermatogenesis in mammals, birds and humans for the treatment and prevention of infertility.

In the preferred embodiment, the invention relates to the compound comprising the antigenic determinant of somatostatin KNFFWKTFTS (SEQ ID NO: 1) as part of fusion recombinant proteins to accelerate the onset of growth of resting follicles, folliculogenesis and spermatogenesis in mammals, birds and humans, for the treatment and prevention of infertility, when active component thereof is administered to mammals, birds or humans.

In the more preferred embodiment, the invention relates to the compound comprising the antigenic determinant of somatostatin KNFFWKTFTS (SEQ ID NO: 1) as part of fusion recombinant proteins to accelerate the onset of growth of resting follicles, folliculogenesis and spermatogenesis in mammals, birds and humans undergoing assisted reproductive treatment for the therapy and prevention of infertility.

The present invention provides an immunogenic composition of compound, comprising the antigenic determinant of somatostatin KNFFWKTFTS (SEQ ID NO: 1) and its analogs, and methods for treatment infertility in patients (mammals, birds and humans) which require such treatment option.

In one embodiment, the invention provides novel polypeptides and polynucleotides encoding thereof, including SSTad polypeptide, fused to a carrier protein through a functionally optimized spacer. The fusion polypeptides of the invention provide highly effective and inexpensive materials for use in the treatment of infertility. A special role in this invention, not disclosed in the above-mentioned analogs, is played by a carrier protein (GBD), which performs a number of functions: a carrier protein for protecting low molecular weight SSTad from proteases, an affinity domain for purifying a fusion protein on a polysaccharide sorbent and an immobilizing domain on a high molecular weight polysaccharide for enchancing the antigen and increasing its immunogenicity.

The spacer sequences used are optimized in length and composition to ensure efficient expression of SSTad fused to the carrier protein in various microorganisms, in particular in *E. coli*. The new spacer sequences provide increased protease resistance and an optimal effect of SSTad on the patient's immune system. They promote the formation of the native U-shaped structure of the SSTad, which the SST has between the two cysteines, and expose it to the outside in the fusion protein, thereby forming an immunodominant epitope.

In another embodiment, the present invention provides novel adjuvant compositions used in the treatment of patients with infertility. In one particular application, the SSTad compound can be combined with novel adjuvants and used in the treatment of infertility or oocyte deficiency conditions or conditions such as sperm deficiency in males or for the prevention of these diseases. The adjuvants in this application are intended for optimal use in mammals, animals, birds, and in particular humans. The adjuvants in this application provide increased immunogenicity of the antigen, allowing lower amounts of antigen to be included in vaccines and higher titers of SST specific antibodies to be reached.

In another embodiment of the invention, pharmacological compositions are provided that result in immunogenicity against SSTad, which initiates the production of specific antibodies, binding of antibodies to SST and a decrease in its content in the blood. This eliminates the inhibition that SST exerts on follicular release and maturation as well as on spermatogenesis. The vaccine formulation options in the present invention are optimized for both safety and achieving the desired effect for high immunogenicity of the SSTad construct in safe and highly effective adjuvant formulations. Vaccines of the present invention require lower amounts of antigen (compared to the concentration of antigen in traditional subunit vaccines), have an increased shelf life and lower cost.

The present invention is focused on the treatment of infertility in humans and other vertebrates. These include mammals and birds in which it is required to restore the number of maturing follicles and the quality of sperm.

The following definitions are provided to facilitate understanding of certain terms often used in the present invention and are not intended to limit the scope of the present disclosure.

Definitions

"Patient" refers to a vertebrate warm-blooded animal, usually a mammal or bird, in need of a composition and/or method of the present invention, for example, a human (female) in need of recovery or an increase in the number of maturing oocytes, or a human (male) in need of recovery or an increase in sperm production and its quality.

"Treatment" refers to the improvement in a patient's condition compared to an untreated patient in a relatively identical or baseline situation. Treatment usually indicates that the desired pharmacological and/or physiological effect has been achieved using the compositions and methods of use thereof of the present invention. Treatment may include prophylactic use of the invention results.

As used herein, the term "infertility treatment" refers to the treatment of a disease or condition, related to the health of the female reproductive system, selected from the group of symptoms, consisting of ovarian failure, premature ovarian failure, infertility, anovulation, infertility characterized by "poor ovarian response" to gonadotropin therapy, delayed puberty, infertility associated with elevated FSH levels, pretreatment with IVF and ART (assisted reproductive technology), spontaneous premature ovarian failure (early menopause), polycystic ovarian disease (fewer growing follicles), and low response (poor response) to COS (controlled ovarian stimulation).

The term "infertility treatment" also refers to the treatment of diseases, associated with the health of the male reproductive system, selected from the group of parenchymal infertility associated with the density and motility of sperm below normal, secretory disorders of spermatogenesis, primary or secondary failure.

The term "ovarian reserve" or "ovarian follicular reserve" is used to describe the number of primary follicles remaining in the ovaries.

The term "resting primordial follicles" is used to describe dormant follicles or primordial follicles from the ovarian reserve. The present invention also relates to a composition and/or method for use thereof provided in the present invention to accelerate the maturation of follicles from the follicular reserve in the treatment of infertility.

"Primary follicle (awakened)" is a rounded formation in the mammalian ovary, consisting of a first-order oocyte surrounded by a zona pellucida, several layers of cubic follicular cells and connective tissue. The primary follicle is three to four times larger than the primordial.

The "secondary follicle" is ten times larger than the primordial one. A cavity with follicular fluid is formed around the oocyte, which reaches a diameter of 2.5 centimeters. Follicular cells form their own complicated, two-layer structure.

"Amino acid" refers to any of the twenty naturally occurring proteinogenic amino acids as well as any modified amino acids.

"Protein" and "peptide" are used to mean an amino acid polymer or a set of two or more interacting or linked amino acid polymers.

An "antigenic determinant" or "epitope" is part of an antigen macromolecule that is recognized by the immune system (antibodies, B lymphocytes, T lymphocytes). The part of an antibody that recognizes an epitope is called a paratope. Although epitopes usually refer to molecules that are foreign to a given organism (proteins, glycoproteins, polysaccharides, etc.), the regions of its own molecules recognized by the immune system are also called epitopes. Most of the epitopes recognized by antibodies or B cells are three-dimensional structures on the surface of antigen molecules (conformational epitopes), which exactly coincide in the shape and spatial arrangement of electric charges and hydrogen bonds with the corresponding antibody paratopes.

"Isolation" refers to a polynucleotide or polypeptide that has been separated or recovered from at least the degradation products of the cell of the producer strain. Purification of the polypeptide from contaminating cell components and polypeptides can be accomplished using any set of well-known methods, including precipitation with ammonium sulfate or ethanol, anionic or cation exchange chromatography, hydrophobic interaction chromatography, and affinity chromatography.

"Antibody" refers to a Y-shaped molecule having a pair of antigen binding sites, a hinge region and a constant region.

"Vaccine" refers to any composition that can stimulate the immune system of a vaccinated subject to generate antibodies to SST for the purposes described herein.

Somatostatin

SST is a peptide hormone that inhibits, among other things, the release of growth hormone from the anterior pituitary gland. SST regulates various endocrine functions by interacting with G-protein-coupled SST receptors on target endocrine cells. SST is secreted from areas of the hypothalamus, stomach, intestines, and pancreas. Controlling the SST level in patients is of interest for increasing the productivity of mammals and birds, changing feeding behavior, and increasing folliculogenesis and spermatogenesis. The effect of SST on the reproductive system is described in the present invention.

In studies, productivity of mammals was optimized by SST vaccination. Overall, SST-immunized farm animals had a weight gain of 8-17%, appetite decreased by 9%, and food efficacy increased by 11%. Animals immunized with SST and their offspring had the correct proportions and the same distribution of animal weight between muscle, bone and fat as in control animals (Reichlin, 1987, Lab Clin Med. 109 (3): 320-326). Thus, these studies indicate that the induction of autoimmunity to SST in the target animal can provide safe and effective results.

SST is known to exert an inhibitory effect on a large number of hormones involved in growth, assimilation of food by animals, and regulation of the reproductive system. As previously described in U.S. Pat. No. 6,316,004 and U.S. patent application Ser. No. 12/195,979, SST and SST fusion variants can be used to immunize animals to increase daily weight and, if necessary, for milk production. These immunization procedures were performed with traditional adjuvants. SST immunization has also been used to treat endogenous growth hormone deficiency (Haffer EP 2291194 B1). SSTad immunization has not previously been used to treat infertility.

The present inventors have obtained an unexpected and reproducible result demonstrating that the modified SST antigen, immunogenic compositions comprising SSTad and vaccination can be used to treat diseases or physiological conditions in a patient, and in particular to treat and prevent infertility.

Advantages

Embodiments of the present invention provide SSTad based methods for the treatment and prevention of infertility in vertebrates and, in particular, in mammals and birds. Exemplary embodiments of the invention are directed to the treatment of humans, mammals and birds. Humans, other mammals and birds are treated with the vaccines of the present invention (see below) to limit or inhibit the effects of endogenous SST on the reproductive system. Vaccines of the present invention will result in additional folliculogenesis and spermatogenesis. Vaccines comprising SSTad and adjuvants are optimized for use in vertebrates and, in particular, for the treatment of human diseases that cause infertility.

Since SST is a highly conserved hormone in vertebrates, embodiments of the present invention are useful for eliciting an immune response in all target vertebrates vaccinated using the methods and compositions described herein. A significant advantage of the present invention is that in vaccinated patients it can take several weeks to several months between booster immunizations, which allows the patient's immune system to bind SST, reduce its concentration and/or remove it from the body for a long time.

The technical aspects of the present invention facilitate all stages of the production and use of the SSTad vaccine, providing a simple and effective technique for obtaining the SSTad substance and producing highly immunogenic composition for use in the prevention and treatment of infertility. This compound for SSTad based immunization was optimized both for expression in producer cells, for the technique of purification and the formation of the native SST conformation, and for the formulation of an immunogenic composition.

In all variants of genetically engineered constructs, SSTad is expressed as codon-optimized chimeric carrier protein, spacer, and SSTad. The carrier protein, due to its binding to polysaccharide sorbents, provides a simple and effective technique of purification from other bacterial proteins, lipopolysaccharides and DNA of the producer strain. Antigens based on the SSTad according to the present invention, due to the binding of the carrier protein to high-polymer soluble polysaccharides, provides the formation of molecular complexes of a larger size (20-40 nm), providing immunogenicity and resistance to degradation by proteases. Thus, the SSTad of the present invention is present in the form of the immunogenic composition in the tissues of the patient for a longer time, causing a greater effect on the patient's immune system. As will be described in more detail below, the present invention also provides a maximized immune response due to optimized adjuvants.

New Vaccine Options for Use in Infertility Treatment

Somatostatin has two active forms that are produced by alternative cleavage of the propeptide, somatostatin-28 and somatostatin-14. However, the amino acid sequence of the tetradecapeptide that binds to the SST receptors is the shorter peptides KNFFWKTFTS (SEQ ID NO: 1), NFFWKTFT (SEQ ID NO: 7), FFWKTF (SEQ ID NO: 8), and FWKT (SEQ ID NO: 9), as confirmed by numerous synthetic SST analogues (Heidarpour et al., 2019, J Res Med Sci. 26: 24-29). FWKT (SEQ ID NO: 9) is a key sequence required for specific receptor binding. Therefore, FWKT (SEQ ID NO: 9) is the minimum key epitope for neutralization of the interaction of SST with the receptor by antibodies. However, using recombinant protein technology, it is very difficult to reproduce the U-shaped conformation of such a short peptide (FIG. 2).

The KNFFWKTFTS (SEQ ID NO: 1) sequence is highly conserved among vertebrates (Lin et al., Comp. 1998, Biochem. Physiol. C. Pharmacol. Toxicol. Endocrinol. 119 (3): 375-388) and, as shown in this invention, is optimal for establishing a specific immune response.

The polysaccharide binding domain can be attached to the SSTad through a variable length spacer. The spacer is necessary to ensure the presentation of the encoded somatostatin on the surface of the protein molecule, as well as optimal presentation to the patient's immune system. Spacer variants used within the present invention provide efficient formation of the U-shaped SST conformation, increased protease resistance and optimal effect on the epitope, and have shown unexpected additional improvement over constructs, lacking a spacer sequence and/or comprising other spacer sequences different from those provided herein.

Spacer variants have been optimized in length and composition to ensure efficient expression of SSTad fused with the carrier protein in a variety of microorganisms, in particular E. coli. As noted above, these new spacer sequences provide increased resistance to proteases (thus providing increased antibody production over that of the constructs disclosed in U.S. Pat. No. 6,316,004) and optimal effects on the patient's immune system. Said combination of SSTad, attached to the polysaccharide binding domain using optimally configured spacer, shows an unexpected improvement in immunization of target patients to increase folliculogenesis and spermatogenesis, compared to immunization with Sat-Som. These constructs are intended to be used as antigens comprising SSTad in the treatment of infertility.

Above-described SSTad recombinant fusion proteins exhibit high storage stability. In addition, the SSTad-based antigens according to the present invention provide a deposition function and a longer half-life in a patient taking into account the increased resistance of these materials to degradation. It is noted that other carrier polypeptides can replace the polysaccharide binding domain for attachment to the SSTad. For example, SSTad can be combined with KLH, tetanus toxoid, CRM 197, chloramphenicol acetyltransferase, or other protein carriers.

Embodiments of the invention also provide novel adjuvant compositions for enhancing the induction of humoral immunity in a target patient. These adjuvant compositions provide a significant improvement over traditional (aluminum hydroxide, oil) for the induction of a humoral response and are safe for use in humans, mammals and birds. Adjuvant compositions are used herein with SSTad based antigens to prepare vaccines of the present invention.

In one embodiment of the invention, the immunological adjuvant comprises dextran-500 to bind a carrier protein and form high-polymer, polysaccharide-soluble molecular complexes of larger size (20-40 nm) that provide immunogenicity and resistance to protease degradation. DEAE-dextran-500 binds CpG oligonucleotides and provides their resistance to nuclease degradation. In more detail, the complex is prepared using CpG oligonucleotide 1585 for animals and CpG oligonucleotide 2216 for humans. CpG oligonucleotides are prepared by oligonucleotide synthesis. In some embodiments of the invention, monophosphoryl lipid A, muramyldipeptide, polymuramil, or other ligands of toll-like receptors can be used, but the use of CpG oligonucleotide is more preferable in the treatment of infertility. It is possible to use the immunogenic composition without CpG oligonucleotide, but achieving a comparable result in the treatment of infertility will require significantly higher amounts of the SSTad fusion protein and a longer immunization schedule. CpG oligonucleotides are dissolved in saline. Adjuvant compositions are combined with the recombinant SSTad fusion protein to prepare vaccines of the invention (Example 5).

In yet another embodiment, the immunological adjuvant comprises Montanide™ (Examples 6, 7, 8) or aluminum hydroxide (Example 9). Adjuvants are combined with the SSTad fusion polypeptides to produce vaccines of the invention. The adjuvants used in the present invention are safe and effective for use in mammals, birds and humans, and are free from animal products and carcinogenic compounds.

The specific combination of adjuvants and concentrations are shown below.

Vectors and Host Cells

The present invention also relates to vectors, containing the polynucleotide molecules of the invention, as well as host cells, transformed with such vectors. Any of the polynucleotide molecules within the invention can be linked to a vector, which typically comprises a selectable marker and replication site, for the corresponding producer cell. Producer cells are genetically engineered to replicate these vectors and thereby express the proteins of the invention. Typically vectors in the examples provided comprise polynucleotide molecules of the present invention, operably linked to suitable transcriptional or translational regulatory sequences, such as sequences for bacterial or viral host cells. Examples of regulatory sequences include transcriptional promoters, operators, mRNA ribosome binding sites, and corresponding sequences that control transcription and translation. Nucleotide sequences are operably linked when the regulatory sequences in the present invention are operably related to polynucleotides encoding the fusion polypeptide of the present invention.

Typical vectors include plasmids, yeast shuttle vectors, baculovirus, modified adenovirus, etc. In one embodiment, the carrier is a modified pET30 plasmid. Host cells for use in the present invention include bacteria such as *E. coli*, yeast, SF-9 insect cells, mammalian cells, plants, etc.

In one embodiment, the regulatory sequences include a T7lac, Trp or T5 promoter for expressing the fusion proteins of the invention in *E. coli* or other prokaryotic cells. These regulatory sequences are widely reported and used in appropriate and distinct conditions. Various plasmids of the present invention have been designed to express the fusion proteins of the present invention using regulatory sequences. Plasmids with the T7lac promoter are preferred.

Host cells for the expression of the targeted fusion proteins include prokaryotic, yeast, and higher eukaryotic cells. Illustrative prokaryotic hosts include cells from bacteria of the genera *Escherichia, Salmonella* and *Bacillus*, as well as the genera *Pseudomonas* and *Streptomyces*. In an exemplary embodiment, the host cell belongs to the genus *Escherichia* and may be *Escherichia coli* (*E. coli*). As shown in the examples below, the constructs of the invention provide optimal expression of the SSTad, which is spacer coupled to the polysaccharide-binding domain under a variety of conditions. These constructs are especially effective in terms of expression in prokaryotic host cells and in particular in bacteria of the genus *Escherichia*.

In one embodiment, *E. coli* cells are transformed with pET plasmid, containing the SSTad fusion protein gene, having suitable regulatory sequences for expression in *E. coli* cells. In some cases, fermentation of approximately ten liters of these cells results in at least 100 grams of total biomass, which then gives approximately 10 grams of total protein. By staining with silver and Coomassie blue, a quarter of the protein mass is the target protein.

Purification of GBD-SSTad-SSTad Fusion Protein

The fusion protein can be purified in accordance with routine protein purification technologies, including, for example, lysis of bacterial cells with the enzyme lysozyme, DNA disruption in French-press modules, using ultrasound or DNAse, subsequent differential centrifugation of inclusion bodies, dissolution of inclusion bodies in guanidine chloride or urea, refolding procedures, column chromatography on affinity and ion exchange columns, and the like.

Aspects of the present invention include the production of an endotoxin-free immunogenic fusion protein. In some embodiments, the fusion protein is produced in a substantially endotoxin-free state. Additional purification completely removes or reduces the concentration of endotoxin to acceptable levels for human use in accordance with pharmacopoeia standards. As such, some of the embodiments of the technique disclosed herein allow achieving the production of substantially endotoxin-free fusion proteins for use in vaccines. In some embodiments, endotoxin levels are at or below 1 EU/ml, and in other embodiments, endotoxin levels are eliminated, that is, the fusion proteins of the present invention are substantially free of endotoxins.

The concentration of the purified fusion protein ranges from 1 to 8 mg/ml and typically from 4 to 6 mg/ml. In some instances, the substantially endotoxin-free chimeric protein is used in the vaccine compositions at a dose of about (1.5 to 5 mg) per 2 ml, and more typically at a dose of (2.0 to 3.5 mg) per 2 ml.

Vaccines

Vaccines in this invention are combinations of immunological adjuvants, as described herein, and antigens, necessary for the prevention or treatment of a patient's condition associated with infertility.

A pharmaceutical dosage for an embodiment of the vaccine as used herein comprises 1-5 mg of the recombinant fusion protein. In all embodiments, the vaccine must be sterile, stable under the conditions of manufacture and storage. Prevention of the growth of the number of microorganisms can be achieved by the addition of various antibacterial and antifungal agents, for example, benzyl alcohol, parabens, chlorobutanol, sorbic acid, thiomersal, and the like.

The adjuvants of the present invention are combined with the SSTad fusion polypeptide to provide a vaccine useful for the treatment of diseases and/or conditions associated with infertility.

Vaccines of the invention typically comprise the SSTad antigen in an amount of recombinant protein from 1 mg/ml to 10 mg/ml dose.

Dextran 500 from 1 mg/ml to 10 mg/ml dose,

DEAE-dextran 500 from 0.2 mg/ml to 2 mg/ml dose, Monophosphoryl lipid A, muramyldipeptide and/or CpG oligonucleotide 1585 from 0.02 mg/ml to 0.2 mg/ml.

Vaccine solutions of the invention are prepared by mixing materials in the required quantities and volumes (antigen, adjuvant, other ingredients), and final sterilization using ultrafiltration. Alternatively, the vaccine solutions of this invention can be prepared using individually sterilized components prior to final formulation.

Vaccines of this invention can be prepared in the form of sterile lyophilized preparations comprising CpG (Example No. 5), oil emulsion with Montanide™ (Examples No. 6, 7, 8) or suspension with aluminum hydroxide (Example No. 9). These preparations are stable under the conditions of manufacture and storage. Embodiments of vaccines in accordance with the invention may further comprise dispersing or wetting agents, suspending agents, or other similar materials.

Method for Treatment of the Patient's Diseases

The described invention provides pharmaceutical grade vaccines, comprising the SSTad fusion proteins and the adjuvants within the invention. Such vaccines can be administered to patients with infertility.

The vaccines of the present invention are intended for the treatment of infertile patients. In one embodiment, the vaccine of the present invention was applied 2 times, however, the number of injections may be increased to 3-5 boosters upon the discretion of the medical professional or veterinarian. Typical amounts of the vaccine antigen are 50-100 µg/ml of fusion recombinant protein per kg of patient weight. The vaccines can be administered by routine methods. In one embodiment, the vaccine is administered by subcutaneous injection (Examples No. 5, 6, 7, 8). In another embodiment, the vaccine is administered by intramuscular injection (Example No. 9).

The progress of treatment in patients, receiving the vaccine formulation according to the invention should be monitored with additional administrations provided upon necessity. The elevation of the growth hormone and anti-SST antibodies levels are target indicators for monitoring treatment efficacy. Based on individual patient's observation of, additional vaccine injections may be administered with adjustable quantity of the SST antigen in accordance with the present invention. In addition, alternative adjuvant combinations may be used to alter the response of a particular patient to vaccination as determined by the medical professional or veterinarian.

The proposed treatment options may be combined with other conventional infertility treatments. For example, the vaccination contemplated by the invention may be combined with conventional hormone therapy strategies.

In general, the described invention will be easier to assess by referring to the following examples.

EXAMPLES

The solution to the problem of cloning, production and purification of recombinant GBD-SSTad-SSTad protein is provided by the following means and methods.

Recombinant protein having a molecular weight of 39.5 kDa, comprises 2 fragments of the antigenic determinant of somatostatin (SSTad) with the sequence SEQ ID NO 1, spacer 1 Gly-Ser with the sequence SEQ ID NO 2, spacer 2 aiming the formation of the U-shaped conformation of SST with the sequence SEQ ID NO 3, the alpha-glucan binding domain (GBD) of a gene from *Streptococcus mutans* with the sequence SEQ ID NO 4. This recombinant protein is encoded by the nucleotide sequence of the GBD-SSTad-SSTad gene SEQ ID NO 5.

A method for producing recombinant GBD-SSTad-SSTad protein on glucan comprises:
  growing *E. coli* cells, expressing the GBD-SSTad-SSTad gene;
  binding of GBD-SSTad-SSTad protein in the composition of cell extracts of *E. coli* BL21 strain to a glucan-containing sorbent due to affinity interaction during the incubation procedure;
  subsequent washing from unbound bacterial proteins and isolation of the desired product.

Recombinant GBD-SSTad-SSTad protein comprises protein sequence of the glucan binding domain, which determines the ability of this protein to bind to the glucan-containing sorbent, which allows to achieve the one-stage concentration, purification, and immobilization of the protein product on glucan. Immobilization on glucan is provided due to the presence of glucan-binding domain from the alpha-glucan-binding domain of the gene from *Streptococcus mutans* in the recombinant protein/. The described domain demonstrates high affinity for alpha-glucans (pullulan, glycogen, dextran, starch) and provides irreversible binding to the carrier in a wide range of pH values 6.0-9.0 and salt concentrations 0-3 M NaCl.

Since *E. coli* cells lack proteins that bind to alpha-glucan, the recombinant GBD-SSTad-SSTad protein synthesized in cells is the only protein of the producer strain that strongly binds to alpha-glucan. This provides the means for a one-step production of a highly purified recombinant protein preparation immobilized on a glucan-containing sorbent.

An injectable preparation for enhancing folliculogenesis and spermatogenesis in mammals, birds and humans comprises recombinant GBD-SSTad-SSTad protein, as described above, suspended in a medium, consisting of a glucan-containing sorbent in a liquid carrier suitable for injection. The method of increasing the folliculogenesis and spermatogenesis in mammals, birds and humans comprises: two time, with an interval of 14-20 days, subcutaneous or intramuscular injections of a preparation, containing recombinant GBD-SSTad-SSTad protein suspended in the medium, consisting of a glucan-containing sorbent in a liquid carrier suitable for injection, at a dose of 5-200 μg of the described protein per kilogram of the patient's body weight.

Therefore, the provided bifunctional recombinant GBD-SSTad-SSTad protein is, capable to bind spontaneously to a glucan-containing sorbent, forming a highly immunogenic composition in the form of polyantigen, to induce the synthesis of specific autoantibodies to SST when administered to patients and consequently stimulating folliculogenesis and spermatogenesis.

Example 1. Preparation of Recombinant GBD-SSTad-SSTad Fusion Protein

At the first stage, the gene of the antigenic determinant of somatostatin is obtained, followed by its cloning. The SSTad gene was obtained by a chemical-enzymatic method. An oligonucleotide duplex was obtained, encoding the corresponding gene, and optimized for expression in *E. coli*. Then GBD-SSTad-SSTad plasmid was obtained comprising the sequences encoding somatostatin, spacer and glucan binding domain (GBD).

Example 2. Preparation of *E. coli* Strain Producing Recombinant Somatostatin Antigen Coupled to Glucan Binding Domain To obtain *E. coli* strain producing recombinant GBD-SSTad-SSTad protein, *E. coli* BL21 cells were transformed by the pGBD-SSTad-SSTad plasmid. 3 μl of 0.1 M solution of isopropyl-beta-O-thiogalactopyranoside (IPTG) was added to the culture and mixture was incubated for 3 hours at 37° C. When comparing the range of proteins synthesized by cells of the *E. coli* BL21 [pGBD-SSTad-SSTad] strain, an additional protein band was found. The molecular weight, corresponding to the additional band was consistent with the 39.5 kDa expected for recombinant GBD-SSTad-SSTad protein. The level of protein synthesis in *E. coli* was determined by comparing the intensity of staining of the band of the recombinant protein with the band of the corresponding protein standard molecular weight. It was shown that recombinant GBD-SSTad-SSTad protein is synthesized in *E. coli* cells in an insoluble form as inclusion bodies.

Example 3. Obtaining of Recombinant GBD-SSTad-SSTad Protein Immobilized on Alpha-Glucan To obtain the recombinant protein, *E. coli* BL21 [pGBD-SSTad-SSTad] cell culture was grown in 1000 ml of LB medium (Luria broth) with ampicillin (100 μg/ml) at 37° C. to an optical density corresponding to 1 unit absorption at a wavelength of 550 nm. 15 μl of 0.1 M IPTG solution was added to the medium and incubated for 3 hours. The cells were sedimented by centrifugation at 5000 g for 15 minutes.

The pellet was resuspended in phosphate buffer containing lysozyme. Additionally, the suspension was sonicated. After centrifugation at 6000 g, insoluble GBD-SSTad-SSTad protein remained in the sediment. The precipitate was suspended in 8 M urea, centrifuged at 12000 g for 30 minutes, and the supernatant was collected. To immobilize recombinant GBD-SSTad-SSTad protein on the sorbent, the supernatant was diluted four times with phosphate buffer, 1/10 of the volume of the alpha-glucan suspension was added, and incubated at 25° C. for 2 hours. The mixture was centrifuged at 8000 g, the pellet was resuspended in phosphate buffer; and alpha-glucan washing was repeated 3 times. The GBD-SSTad-SSTad antigen immobilized on alpha-glucan is a suspension of the sorbent with the protein adsorbed thereon. The purity of the preparation was at least 95%. The preparation was preserved by adding benzyl alcohol to a final concentration of 0.1% (by volume).

Example 4. Biological Effects of Recombinant GBD-SSTad-SSTad Protein

In a preferred embodiment of the invention, the preparation comprises recombinant GBD-SSTad-SSTad protein, lyophilized with the necessary excipients and CpG oligonucleotide or suspended in water oil suspension of Montanide™ (50% by weight) or aluminum hydroxide, and administered by subcutaneous or intramuscular injection of the preparation twice with an interval between injections of 20 days at a dose of 5-200 µg of recombinant protein per kilogram of body weight of an animal or bird. The mechanism of action of the drug is based on temporary blocking of the activity of endogenous SST by autoantibodies.

ogy of the ovaries of rodents and women, makes the mouse a useful model for studying the regulation of ovarian function, fertility aneurysm and ovarian reserve (Dixon et al., 2014, J Toxicol Pathol, 27 (3-4 Suppl); Cora et al., 2015, Toxicol Pathol., 43 (6): 776-793). According to the results of the above study, the applicants unexpectedly found that by inducing the synthesis of specific autoantibodies to SST, it is possible to suppress the responses of the SST receptors, which leads to a pharmacological effect on the ovarian reserve of the ovaries and, as a consequence, accelerates the onset of growth of resting follicles. This effect contributed to an increase in the number of primary and secondary follicles in comparison with those in the control group of animals.

The biological activity of the resulting immunogenic composition was investigated using subcutaneous injections twice with an interval of 20 days at a dose of 50 µg of recombinant protein per animal. The lyophilized vaccine preparation was suspended in saline and injected subcutaneously.

Table 1 shows the results of the enzyme-linked immunosorbent assay (ELISA) of blood in the form of antibody titers. In this case, a comparison was made of the obtained antibody titers in blood samples of mice after immunization with four vaccine compositions using the recombinant GBD-SSTad-SSTad as antigen, with various adjuvants in each case. Vaccines differed in the absence or presence of molecular adjuvants, which were monophosphoryl lipid A, muramyldipeptide and CpG oligonucleotide 1585. A group of 5 mice was allocated for each composition. According to the results obtained in each group, the average values of the ELISA dilution parameters (titer) were derived. The highest value, equal to $6 \times 10^4$, was obtained in the group of mice immunized with the composition comprising the CpG oligonucleotide. The lowest value, equal to $2 \times 10^3$, was found in the group of mice immunized with the composition comprising only dextran. Based on the data obtained, it can be concluded that the most striking immune response is elicited by the composition using the CpG oligonucleotide as an adjuvant.

TABLE 1

| | | | \multicolumn{5}{c|}{ELISA dilution parameters (antibody titers)} | |
|---|---|---|---|---|---|---|---|---|
| Antigen composition components | Number of immunizations | Method of administration | \multicolumn{5}{c|}{The value of the dilution parameters in ELISA (titer)} | ELISA average (titer) |
| | | | mouse 1 | mouse 2 | mouse 3 | mouse 4 | mouse 5 | |
| GBD-SSTad-SSTad | 3 | subcutaneously | $1 \times 10^3$ | $1 \times 10^3$ | $2 \times 10^3$ | $1 \times 10^3$ | $2 \times 10^3$ | $2 \times 10^3$ |
| GBD-SSTad-SSTad, MPLA | 3 | subcutaneously | $1 \times 10^4$ | $2 \times 10^4$ | $1 \times 10^4$ | $1 \times 10^4$ | $1 \times 10^4$ | $1 \times 10^4$ |
| GBD-SSTad-SSTad, MDP | 3 | subcutaneously | $2 \times 10^4$ | $1 \times 10^4$ | $1 \times 10^4$ | $2 \times 10^4$ | $1 \times 10^4$ | $1 \times 10^4$ |
| GBD-SSTad-SSTad, CpG | 3 | subcutaneously | $4 \times 10^4$ | $5 \times 10^4$ | $6 \times 10^4$ | $7 \times 10^4$ | $8 \times 10^4$ | $6 \times 10^4$ |

The following examples illustrate the efficacy of the use of the preparation for enhancing the activity of folliculogenesis and spermatogenesis in mammals, birds and humans.

Example 5

To describe the in vivo action of the injectable preparation with the SST antigenic determinant and to determine its effect on the development of the primary follicle, the patent applicants conducted studies on an in vivo mouse model. The close similarity of the reproductive system, especially regarding ovarian morphology, physiology and endocrinol- GBD-SSTad-SSTad is recombinant protein, Dextran 500, DEAE is Dextran 500, MPLA is monophosphoryl lipid A, MDP is muramyldipeptide, CpG is oligonucleotide.

Results of Histological Examination

Despite the differences in the values of the ELISA dilution parameters when using compositions with various kinds of adjuvants, the follicular response was approximately at the same level in all groups of mice studied.

According to the results of a histological examination of the ovaries of mice immunized with GBD-SSTad-SSTad using the previously studied compositions, a significant increase in the number of follicles was found from the mean value in the control group, which is equal to from 11.1 to 18.8 in the group of vaccinated mice corresponding to 69% increase. This parameter includes the total number of all follicles: from primordial to vesicular and Graaf vesicles and characterizes an increase in the rate of their differentiation, which result can be considered as a positive effect on folliculogenesis.

The total number of structural and functional elements also increased from an average value of 25.8 in the control group to 43.1 in the groups after vaccination. The percentage of growth is 67. This value includes, in addition to follicles, also atretic elements and corpora *lutea*. The latter are formed in the luteal phase after the release of the oocyte, in extremely rare cases luteinization of unovulated follicles was observed, and respectively, this parameter can be interpreted as the number of mature oocytes released. In the control group, the average number of corpora *lutea* was 8.2. In the test groups, this value was 13.3 (an increase of 62%), which indicates a positive effect of immunoneutralization of endogenous SST on an increase in oocytes release during ovulation.

Atretic elements, which are formed at different stages of folliculogenesis, are follicles that have not reached the stage of a mature Graaf bubble and follicles undergoing destructive changes. Increasing in the number of such elements is also observed after immunoneutralization, from 6.5 in the control to 11.0 in the test groups (an increase of 69%), which fits into the value of an increase in follicles and a general increase in the number of structural and functional elements of the ovaries.

TABLE 2

Morphofunctional assessment of the effect of the GBD-SSTad-SSTad preparation on the ovary

| Parameter | Control | GBD-SSTad-SSTad CpG | Increase compared to control (%) |
|---|---|---|---|
| Primary follicles | 1.8:(0.5-3.1) | 4.3:(2.6-6.0) | 80 |
| Secondary follicles | 1.8:(1.4-2.2) | 2.8:(1.1-4.5) | 56 |
| Tertiary (early atrial follicle) | 3.2:(2.3-4.1) | 4.2:(2.9-5.5) | 31 |
| Vesicular follicle with and without cumulus oophorus, with and without oocyte, and with little fluid | 1.1:(0.7-1.5) | 2.8:(1.5-4.1) | 154 |
| Follicles (from primordial to quaternary) | 11.1:(9.4-12.8) | 18.8:(15.4-22.2) | 69 |
| Corpora lutea | 8.2:(4.8-11.6) | 13.3:(11.6-15.0) | 62 |
| Interstitial glands (corpora atretica) and atretic follicles | 6.5:(2.7-7.8) | 11.0:(8.0-14.0) | 69 |
| Atretic follicle and corpora lutea | 14.7:(11.7-17.7) | 24.3:(20.9-27.7) | 65 |
| Total number of structural and functional elements | 25.8:(23.0-28.6) | 43.1:(37.9-48.3) | 67 |

Close values of the studied parameters were obtained in works and patents (Gougeon, 2011, Gynecol Obstet Fertil. 39 (9): 511-3; Gougeon et al., 2010, Endocrinology 151 (3): 1299-309; Gougeon and Loumaye EP 20040791488 08.10.2004; Gougeon US 20070155659 A1 5.7.2007; Tran and Gotteland EP2835136A1 11.02.2015) using SST antagonist analogs.

Example 6

A study of the GBD-SSTad-SSTad preparation was conducted to restore the sexual cyclicity and fertility of dairy cows with ovarian hypofunction.

One of the reasons that hinder the maximum realization of the reproductive and productive potential of highly productive dairy cows is postpartum ovariopathy, the main form of which is ovarian hypofunction, characterized by depression of folliculogenesis and ovulation. Postpartum ovarian dysfunction refers to hypothalamic-pituitary regulation diseases associated with functional shifts in the neuroendocrine system.

The experiment was carried out on 40 infertile cows with clinically pronounced signs of ovarian hypofunction. In animals, persistent anaphrodisia was noted (no resumption of sexual cyclicity for 2.5-3.0 months after childbirth). Transrectal ultrasound examination showed that the ovaries are reduced in size, and the diameter of the growing follicles reaches 6-10 mm.

The experiment was performed on 40 cows, which were divided into 2 groups of 20 cows each. The animals from the first group were injected with GBD-SSTad-SSTad at a dose of 50 µg per 1 kg of live weight (dose selection for large animals is given in Example 3). Recombinant GBD-SSTad-SSTad protein suspended in the medium consisting of alpha-glycan (50% by weight), water oil suspension Montanide™ (50% by weight) was injected twice subcutaneously with an interval of 20 days. Individuals from the second (intact) group were chosen as controls. They were monitored for 3 months.

Within 3 months, in cows of the control group, fertility recovered only in 26.7% of cases, while in animals received the preparation with GBD-SSTad-SSTad protein, fertility recovered in 85.7% of cases (Table 3). The duration of infertility per one cow in the experiment decreased by 1.8 times when using GBD-SSTad-SSTad.

TABLE 3

Efficacy of the preparation comprising GBD-SSTad-SSTad protein in cow's ovarian hypofunction

| Parameter | GBD-SSTad-SSTad group | Control group |
|---|---|---|
| Number of animals, head | 20 | 20 |
| Restored sexual cycling and were inseminated | | |
| number of animals | 19 | 14 |
| % | 95.4 | 74.2 |
| The period from the beginning of observation until the onset of the sexual cycle and insemination, days | 15.0 ± 2.0 | 78.0 ± 18.0 |
| Fertilized | | |
| number of animals | 17 | 6 |
| % | 85.7 | 26.7 |
| Period from the beginning of observation to fertilization, days | 22.7 ± 4.6 | 78.2 ± 20.7 |
| Average number of days of infertility per cow over the observation period | 38.3 | 90.2 |

Therefore, when administered to cows with ovarian hypofunction, GBD-SSTad-SSTad specifically acts on the pituitary-gonadal system, leveling postpartum ovariopathy, characterized by 35uppression of folliculogenesis and ovulation.

Example 7

The efficacy of the preparation in increasing spermatogenesis in stud farm animals at the stage of physiological maturity disconfirmed by the following examples. To select the optimal amount of the drug (dose selection), the GBD- SSTad-SSTad preparation was injected twice with an interval of 20 days to three groups of boars of Large White breed at the dose of 25 or 50 or 100 μg of recombinant protein per 1 kg of live weight. Recombinant GBD-SSTad-SSTad protein was suspended in the medium consisting of alpha-glycan (50% by weight), water-oil suspension Montanide™ (50% by weight) and was injected subcutaneously. Before and after the use of the preparation, sperm was taken from the stud boars, according to the established procedure and the volume of ejaculate, the sperm concentration in the ejaculate and the number of semen doses were determined. The parameters of sperm production in boars when using the drug at a dose of 25 μg per 1 kg of live weight are shown in Table 4. The drug had a positive effect on boar sperm production.

TABLE 4

Parameters of sperm production in boars of Large White breed when using the GBD-SSTad-SSTad preparation at a dose of 25 μg of recombinant protein per 1 kg of live weight (n = 5)

| Sperm quality parameters | Baseline values | Values 30 days after the second injection | Values 60 days after the second injection | Values 90 days after the second injection |
|---|---|---|---|---|
| Ejaculate volume, ml | 215.7 ± 8.9 | 221.9 ± 19.3 | 230.6 ± 16.5 | 229.6 ± 17.3 |
| Sperm concentration, million/ml | 180.6 ± 15.3 | 190.5 ± 19.3 | 195.5 ± 18.5 | 194.1 ± 15.8 |
| Number of semen doses received from one animal | 14 | 16 | 18 | 18 |

According to the data presented in Table 4, the GBD-SSTad-SSTad preparation at a dose of 25 μg of active ingredient per kilogram of live weight resulted a slight increase in sperm production compared to baseline values in boars of Large White breed. The volume of ejaculates increased, depending on the time of control of this parameter (30, 60, 90 days after the second injection of the drug), by 5.9-8.0%. The concentration of sperm in ejaculates increased by 2.8-5.8%, which led to an increase in the number of semen doses received from one animal by 15.4-16.7%.

Sperm production parameters in boars of Large White breed when using the GBD-SSTad-SSTad preparation at a dose of 50 μs of recombinant protein per kilogram of live weight are shown in Table 5.

As follows from the data presented in Table 5, the administration of the GBD-SSTad-SSTad preparation at a dose of 50 μg of active ingredient per kilogram of live weight resulted in a significant increase in sperm production compared to baseline values in boars of Large White breed. The volume of ejaculates of animals increased, depending on the time of control of this parameter (30, 60, 90 days after the second injection of the drug), by 13.9-20.0%.

TABLE 5

Parameters of sperm production in boars of Large White breed when using the GBD-SSTad-SSTad preparation at a dose of 50 μg of recombinant protein per 1 kg of live weight (n = 3)

| Sperm quality parameters | Baseline values | Values 30 days after the second injection | Values 60 days after the second injection | Values 90 days after the second injection |
|---|---|---|---|---|
| Ejaculate volume, ml | 215.9 ± 5.8 | 242.5 ± 18.2 | 254.9 ± 15.5 | 253.5 ± 15.1 |
| Sperm concentration, million/ml | 180.8 ± 15.5 | 205.5 ± 17.7 | 213.3 ± 15.6 | 214.4 ± 14.6 |
| Number of semen doses received from one animal | 14 | 18 | 20 | 20 |

The sperm concentration in the obtained ejaculates of animals increased by 13.2-15.0%, which led to an increase in the number of semen doses obtained from one animal by 26.8-35.6%.

Sperm production parameters in boars of Large White breed when using the GBD-SSTad-SSTad preparation at a dose of 100 μg of recombinant protein per kilogram of live weight are shown in Table 6.

As follows from the data presented in Table 6, administration of the GBD-SSTad-SSTad preparation to animals at a dose of 100 μg of active ingredient (recombinant protein) per kilogram of live weight resulted in an increase in sperm production compared to baseline values in boars of Large White breed. The volume of ejaculates of animals statistically and significantly increased, depending on the time of control of this parameter (30, 60, 90 days after the second injection of the drug), by 14.8-19.3%. The sperm concentration in the ejaculates of animals increased by 8.3-10.7%, which led to an increase in the number of semen doses received from one animal by 21.5-33.0%.

TABLE 6

Parameters of sperm production in boars of Large White breed when using the GBD-SSTad-SSTad preparation at a dose of 100 μg of recombinant protein per 1 kg of live weight (n = 3)

| Sperm quality parameters | Baseline values | Values 30 days after the second injection | Values 60 days after the second injection | Values 90 days after the second injection |
|---|---|---|---|---|
| Ejaculate volume, ml | 214.5 ± 9.7 | 243.3 ± 14.7 | 253.2 ± 13.5 | 254.5 ± 15.6 |
| Sperm concentration, million/ml | 183.5 ± 15.6 | 200.6 ± 16.5 | 211.6 ± 16.7 | 210.8 ± 18.6 |
| Number of semen doses received from one animal | 15 | 17 | 19 | 20 |

Therefore, the experiments carried out in the conditions of an industrial pig-breeding farm to substantiate the most effective dose of the GBD-SSTad-SSTad preparation confirmed pharmacological activity thereof and promising perspective of its use for stimulating spermatogenesis in boars of Large White breed.

When the GBD-SSTad-SSTad preparation is used twice, 50 and 100 μg per kilogram of animal weight, approximately the same biological effect is observed. Therefore, it is advisable to use a dose of GBD-SSTad-SSTad equal to 50 μg/kg of animal weight.

Analysis of boar spermograms showed an increase in spermatogenesis after the administration of the preparation at a dose of 50 µg of protein per kilogram of live weight (Table 7). During the entire observation period, boars showed an increase in the total volume of ejaculates, the sperm concentration and motility, which resulted in a statistically and significantly increased number of semen doses suitable for insemination of breeding sows and young gilts by 25.2% compared to baseline value. In the ejaculates of the animals of the experimental group, 60 days after the administration of the GBD-SSTad-SSTad preparation, an increase in the absolute survival of spermatozoa by 10% from the baseline value was observed.

TABLE 7

Effect of the use of the GBD-SSTad-SSTad preparation on the parameters of sperm production in boars when administering 50 µg of recombinant protein per 1 kg of live weight of animals (n = 5)

| Sperm quality parameters | Baseline value | Values 30 days after the second injection | Values 60 days afterv the second injection |
| --- | --- | --- | --- |
| Ejaculate volume, ml | 210.67 ± 7.5 | 221.33 ± 4.4 | 225.54 ± 6.7 |
| Sperm motility, score | 8.5 | 8.7 | 8.9 |
| Sperm concentration, million/ml | 303.45 ± 15.6 | 307.84 ± 15.6 | 306.54 ± 16.7 |
| Number of semen doses received | 14 | 18 | 20 |
| Absolute sperm survival at 16-18° C., RU (relative units) | 1160 | 1250 | 1290 |

When breeding sows were inseminated with ejaculates obtained from studs received the GBD-SSTad-SSTad preparation, an increase in the fertilizing ability of sperm was found. In the groups of breeding sows inseminated with the sperm of the boar received the preparation, there was a tendency to an increase in multiple pregnancies, including an increase in the number of live newborn piglets by 10%.

Example 8

The preparation comprising recombinant GBD-SSTad-SSTad protein suspended in the medium consisting of alpha-glycan (50% by weight), water oil suspension Montanide™ (50% by weight) was injected to dairy bulls twice subcutaneously with an interval of 20 days at the rate of 50 μg of recombinant protein per 1 kg of live weight of animals. The parameters of sperm production in animals on days 30, 60, and 90 after the second injection of the preparation are presented in Table 8.

TABLE 8

Parameters of sperm production in dairy bulls when using the GBD-SSTad-SSTad preparation at a dose of 50 μg of recombinant protein per 1 kg of live weight (n = 3)

| Sperm quality parameters | Baseline values | Values 30 days after the second injection | Values 60 days after the second injection | Values 90 days after the second injection |
|---|---|---|---|---|
| Ejaculate volume, ml | 3.80 ± 0.18 | 4.25 ± 0.16 | 4.56 ± 0.16 | 5.15 ± 0.16 |

TABLE 8-continued

Parameters of sperm production in dairy bulls when using the GBD-SSTad-SSTad preparation at a dose of 50 μg of recombinant protein per 1 kg of live weight (n = 3)

| Sperm quality parameters | Baseline values | Values 30 days after the second injection | Values 60 days after the second injection | Values 90 days after the second injection |
|---|---|---|---|---|
| Sperm concentration, million/ml | 1.22 ± 0.14 | 1.22 ± 0.12 | 1.20 ± 0.12 | 1.21 ± 0.13 |
| Number of semen doses received from one animal | 616 | 940 | 969 | 980 |

The results of administration of the GBD-SSTad-SSTad preparation indicate its positive effect on sperm production and the quality of bovine sperm. In stud dairy bulls, the volume of ejaculates during the observation period statistically and significantly increased by 12%, the number of semen doses received from one animal increased by 40%, while the percentage of sperm rejects decreased by two. The sperm concentration in the ejaculates of dairy bulls during the observation period remained at the same level.

Example 9

The efficacy of the GBD-SSTad-SSTad preparation for increasing spermatogenesis in roosters at the stage of physiological maturity is illustrated by the following example.

The study of the effect of the preparation on the productive qualities of stud roosters (two-line hybrid of Plymouth Rock and Cornish) was carried out at poultry farms.

The preparation was used at a dose of 50 μg/kg of recombinant GBD-SSTad-SSTad protein suspended in the medium consisting of alpha-glycan, aluminum hydroxide suspension, twice with an interval of 20 days at the rate of 50 μg of recombinant protein per 1 kg of live weight of birds. Before and after the administration of the preparation, sperm samples were obtained from the stud roosters, and the volume of ejaculate, the concentration of sperm in the ejaculate and the number of received semen doses were determined. The parameters of sperm production in roosters when using the preparation at a dose of 50 μg per 1 kg of live weight are shown in Table 9.

TABLE 9

Parameters of sperm production in roosters when using the GBD-SSTad-SSTad preparation at a dose of 50 μg per kg of live weight (n = 5)

| Sperm quality parameters | Baseline values | Values 30 days after the second injection | Values 60 days after the second injection | Values 90 days after the second injection |
|---|---|---|---|---|
| Ejaculate volume, ml | 0.53 ± 0.05 | 0.59 ± 0.02 | 0.74 ± 0.03 | 0.76 ± 0.03 |
| Sperm concentration, million/ml | 2.1 ± 0.05 | 1.98 ± 0.06 | 2.1 ± 0.06 | 2.2 ± 0.04 |
| Number of semen doses received from one animal | 13 | 15 | 19 | 18 |

The results of the experiment confirm the stimulation of sperm production in breeding roosters resulting from the use of the preparation. So the volume of ejaculate taken from roosters 90 days after the first injection increased by 40%. During the period of observation, the quality parameters of the collected sperm in terms of sperm survival improved. The use of the GBD-SSTad-SSTad preparation in stud roosters resulted in an increase in the number of received semen doses by 40% and a decrease in the percentage of sperm rejects based on biological indicators.

The above examples of the implementation of the invention are not limiting. Other embodiments are possible within the scope of the patent claims.

However, according to the studies conducted and attempts to carry out the invention, the present examples demonstrate that an essential feature of the invention are new spacers specially designed to solve the problem of obtaining a highly immunogenic protein for effective vaccination in the framework of the treatment and/or prevention of infertility, improving the quality of oocytes and/or sperm.

During the implementation of the invention, attempts have been made to produce a recombinant protein comprising somatostatin antigenic determinants using spacers other than those of sequence 2 and 3. For example, attempts have been made to use the known spacer ProGlySerGlySerGlySerGlySerGlySerAla (SEQ ID NO: 10). These attempts, both using the specified spacer in combination with one of the spacers according to the invention, and using only the specified spacer, did not lead to the formation of the correct three-dimensional structure of the recombinant protein, which precluded solving the problem. The desired efficacy could not be achieved correspondingly with the technical results indicated in this application, which showed the importance of the optimal selection of the spacer for the recombinant protein to solve the assigned task. Only the spacers developed according to the invention resulted in the formation of U-shaped SSTad structure (which is identical to the somatostatin fragment between two cysteines), as well as exposing this structure to the outside of the fusion protein. Thus, an immunodominant epitope was formed resulting in the development of the preparation based on the recombinant protein, capable to induce a high immune response against somatostatin. In addition, the spacers of the invention provide sufficient proteolytic protection for the antigenic determinant, as illustrated by the examples. All the effects of the invention can only be achieved using the spacers of the invention.

In addition, during the implementation of the invention, the importance of using exactly 2 antigenic determinants was confirmed. The prior patents could not suggest the use of 2 distinct antigenic determinants of somatostatin, since the single one was always used in the previous patents. This technique is also new to the authors of the present invention in relation to other immunogenic antigenic determinants, which shows the originality and novelty of this approach. It should be emphasized that in the process of working on the invention, a recombinant protein was obtained with only one antigenic determinant. Such a recombinant protein did not show the effects characteristic of the claimed group of inventions. Likewise, the use of a determinant different from that used according to the claimed invention did not succeed in solving the assigned tasks.

To summarize the abovementioned facts, we can conclude that the essential features of the invention are the sequences of spacer 1 and spacer 2 according to the invention and the use of two antigenic determinants having the sequence KNFFWKTFTS (SEQ ID NO: 1) to obtain a recombinant protein for the treatment and/or prevention of infertility, as well as increasing folliculogenesis and spermatogenesis in mammals, birds and humans.

```
--->
List of sequences:

Amino acid sequence of the antigenic determinant of somatostatin
<210> 3
<211> 11
<212> PRT
<213> Homo sapience
<400> 3
                                                              SEQ ID NO 1
Lys Asn Phe Phe Trp Lys Thr Phe Thr Ser
1 5 10

Spacer 1 amino acid sequence
<210> 3
<211> 11
<212> PRT
<213> Artifical Sequence
<400> 3
                                                              SEQ ID NO 2
Ser Gly Gly Gly Gly Ser Gly Gly Gly Gly Ser Gly Gly Gly Gly Ser 1 5 10 15 Ala Gly Gly Gly Gly Ser Arg
20

Spacer 2 amino acid sequence
<210> 3
<211> 11
<212> PRT
<213> Artifical Sequence
                                                              SEQ ID NO 3
Ser Gly Thr Gly Ser Gly Glu Ile Ala Ala Leu Glu Gln Glu Ile Ala 1 5 10 15 Ala Leu Glu Lys Glu Asn Ala Ala Leu Glu Trp Glu Ile Ala Ala Leu 20 25 30 Glu Gln Gly Gly Pro Gly Thr Gly-Gly Thr Gly Thr Gly Ser Gly Ala 35 40 45 Lys Ile Ala Ala Leu Lys Gln Lys Ile Ala Ala Leu Lys Tyr Lys Asn 50 55 60 Ala Ala Leu Lys Lys Lys Ile Ala Ala Leu Lys Gln Gly Gly Gly Thr 65 70 75 80 Gly Ser Gly Thr Arg
```

Amino acid sequence of the alpha-glucan binding domain
from *Streptococcus mutans*
<210> 3
<211> 11
<212> PRT <213> *Streptococcus mutans*
<400> 3

SEQ ID NO 4

Met Gly Ser Thr Asn Gln Tyr Tyr Gln Leu Ala Asp Gly Lys Tyr Met
1               5                  10                 15
Leu Leu Asp Asp Ser Gly Arg Ala Lys Thr Gly Phe Val Leu Gln Asp
            20                  25                  30
Gly Val Leu Arg Tyr Phe Asp Gln Asn Gly Glu Gln Val Lys Asp Ala
        35                  40                  45
Ile Ile Val Asp Pro Asp Thr Asn Leu Ser Tyr Tyr Phe Asn Ala Thr
    50                  55                  60
Gln Gly Val Ala Val Lys Asn Asp Tyr Phe Glu Tyr Gln Gly Asn Trp
65              70                  75                  80
Tyr Leu Thr Asp Ala Asn Tyr Gln Leu Ile Lys Gly Phe Lys Ala Val
            85                  90                  95
Asp Asp Ser Leu Gln His Phe Asp Glu Val Thr Gly Val Gln Thr Lys
        100                 105                 110
Asp Ser Ala Leu Ile Ser Ala Gln Gly Lys Val Tyr Gln Phe Asp Asn
    115                 120                 125
Asn Gly Asn Ala Val Ser Ala Arg
130                 135

Nucleotide sequence of the GBD-SSTad-SSTad gene

SEQ ID NO 5

CTCGAGAAAT CATAAAAAAT TTATTTGCTT TGTGAGCGGA TAACAATTAT AATAGATTCA   60

ATTGTGAGCG GATAACAATT TCACACAGAA TTCATTAAAG AGGAGAAATT AACT        114

ATG GGC TCC ACC AAT CAA TAT TAT CAA CTT GCC GAT GGC AAA TAT ATG    162
Met Gly Ser Thr Asn Gln Tyr Tyr Gln Leu Ala Asp Gly Lys Tyr Met
1               5                  10                 15

CTT CTT GAT GAT TCC GGC AGG GCC AAA ACC GGC TTT GTT CTT CAA GAT    210
Leu Leu Asp Asp Ser Gly Arg Ala Lys Thr Gly Phe Val Leu Gln Asp
            20                  25                  30

GGC GTT CTT AGG TAT TTT GAT CAA AAT GGC GAA CAA GTT AAA GAT GCC    258
Gly Val Leu Arg Tyr Phe Asp Gln Asn Gly Glu Gln Val Lys Asp Ala
        35                  40                  45

ATT ATT GTT GAT CCC GAT ACC AAT CTT TCC TAT TAT TTT AAT GCC ACC    306
Ile Ile Val Asp Pro Asp ThrAsn Leu Ser Tyr Tyr Phe Asn Ala Thr
    50                  55                  60

CAA GGC GTT GCC GTT AAA AAT GAT TAT TTT GAA TAT CAA GGC AAT TGG    354
Gln Gly Val Ala Val Lys Asn Asp Tyr Phe Glu Tyr Gln Gly Asn Trp
65              70                  75                  80

TAT CTT ACC GAT GCC AAT TAT CAA CTT ATT AAA GGC TTT AAA GCC GTT    402
Tyr Leu Thr Asp Ala Asn Tyr Gln Leu Ile Lys Gly Phe Lys Ala Val
            85                  90                  95

GAT GAT TCC CTT CAA CAT TTT GAT GAA GTT ACC GGC GTT CAA ACC AAA    450
Asp Asp Ser Leu Gln His Phe Asp Glu Val Thr Gly Val Gln Thr Lys
        100                 105                 110

GAT TCC GCC CTT ATT TCC GCC CAA GGC AAA GTT TAT CAA TTT GAT AAT    498
Asp Ser Ala Leu Ile Ser Ala Gln Gly Lys Val Tyr Gln Phe Asp Asn
    115                 120                 125

AAT GGC AAT GCC GTT TCC GCC AGG TCC GGC GGC GGC GGC TCC GGC GGC    546
Asn Gly Asn Ala Val Ser Ala Arg Ser Gly Gly Gly Gly Ser Gly Gly
130                 135                 140

GGC GGC TCC GGC GGC GGC GGC TCC GCC GGC GGC GGC GGC TCC AGG TCC    594

-continued

```
Gly Gly Ser Gly Gly Gly Gly Ser Ala Gly Gly Gly Gly Ser Arg Ser
145                 150                 155                 160

GGC ACC GGC TCC GGC GAAATT GCC GCC CTT GAA CAA GAAATT GCC GCC        642

Gly Thr Gly Ser Gly Glu Ile Ala Ala Leu Glu Gln Glu Ile Ala Ala
165                 170                 175

CTT GAA AAA GAA AAT GCC GCC CTT GAA TGG GAAATT GCC GCC CTT GAA       690

Leu Glu Lys Glu Asn Ala Ala Leu Glu Trp Glu Ile Ala Ala Leu Glu
180                 185                 190

CAA GGC GGC CCC GGC ACC GGC AAA AAT TTT TTT TGG AAA ACC TTT ACC     738

Gln Gly Gly Pro Gly Thr Gly Lys Asn Phe Phe Trp Lys Thr Phe Thr
195                 200                 205

TCC GGC ACC GGC ACC GGC TCC GGC GCC AAA ATT GCC GCC CTT AAA CAA    786

Ser Gly Thr Gly Thr Gly Ser Gly Ala Lys Ile Ala Ala Leu Lys Gln
210                 215                 220

AAA ATT GCC GCC CTT AAA TAT AAA AAT GCC GCC CTT AAA AAA AAA ATT    834

Lys Ile Ala Ala Leu Lys Tyr Lys Asn Ala Ala Leu Lys Lys Lys Ile
225                 230                 235                 240
GCC GCC CTT AAA CAA GGC GGC GGC ACC GGC TCC GGC ACC AGG TCC GGC    882

Ala Ala Leu Lys Gln Gly Gly Gly Thr Gly Ser Gly ThrArg Ser Gly
245                 250                 255

ACC GGC TCC GGC GAAATT GCC GCC CTT GAA CAA GAAATT GCC GCC CTT      930

Thr Gly Ser Gly Glu Ile Ala Ala Leu Glu Gln Glu Ile Ala Ala Leu
260                 265                 270

GAA AAA GAA AAT GCC GCC CTT GAA TGG GAAATT GCC GCC CTT GAA CAA     978

Glu Lys Glu Asn Ala Ala Leu Glu Trp Glu Ile Ala Ala Leu Glu Gln
275                 280                 285

GGC GGC CCC GGC ACC GGC AAA AAT TTT TTT TGG AAA ACC TTT ACC TCC   1026

Gly Gly Pro Gly Thr Gly Lys Asn Phe Phe Trp Lys Thr Phe Thr Ser
290                 295                 300

GGC ACC GGC ACC GGC TCC GGC GCC AAA ATT GCC GCC CTT AAA CAA AAA   1074

Gly Thr Gly Thr Gly Ser Gly Ala Lys Ile Ala Ala Leu Lys Gln Lys
305                 310                 315                 320

ATT GCC GCC CTT AAA TAT AAA AAT GCC GCC CTT AAA AAA AAA ATT GCC   1122

Ile Ala Ala Leu Lys Tyr Lys Asn Ala Ala Leu Lys Lys Lys Ile Ala
325                 330                 335

GCC CTT AAA CAA GGC GGC GGC ACC GGC TCC GGC ACC AGG TCC TAA CCG   1170

Ala Leu Lys Gln Gly Gly Gly Thr Gly Ser Gly Thr Arg Ser Stop
340                 345                 350

GACTTCGAAG CGTTCGGTTG GGTCCGGAAT TCGTATGGC AATGAAAGAC GGTGAGCTGG
1230

TGATATGGGA TAGTGTTCAC                                              1250
<---
```

SEQUENCE LISTING

<160> NUMBER OF SEQ ID NOS: 11

<210> SEQ ID NO 1

```
<211> LENGTH: 10
<212> TYPE: PRT
<213> ORGANISM: Homo sapiens
<220> FEATURE:
<221> NAME/KEY: misc_feature
<223> OTHER INFORMATION: Amino acid sequence of the antigenic
      determinant of somatostatin

<400> SEQUENCE: 1

Lys Asn Phe Phe Trp Lys Thr Phe Thr Ser
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Spacer 1 amino acid sequence

<400> SEQUENCE: 2

Ser Gly Gly Gly Gly Ser Gly Gly Gly Ser Gly Gly Gly Ser
1               5                   10                  15

Ala Gly Gly Gly Gly Ser Arg
            20

<210> SEQ ID NO 3
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Spacer 2 amino acid sequence

<400> SEQUENCE: 3

Ser Gly Thr Gly Ser Gly Glu Ile Ala Ala Leu Glu Gln Glu Ile Ala
1               5                   10                  15

Ala Leu Glu Lys Glu Asn Ala Ala Leu Glu Trp Glu Ile Ala Ala Leu
            20                  25                  30

Glu Gln Gly Gly Pro Gly Thr Gly Thr Gly Thr Gly Ser Gly Ala
        35                  40                  45

Lys Ile Ala Ala Leu Lys Gln Lys Ile Ala Ala Leu Lys Tyr Lys Asn
    50                  55                  60

Ala Ala Leu Lys Lys Lys Ile Ala Ala Leu Lys Gln Gly Gly Thr
65                  70                  75                  80

Gly Ser Gly Thr Arg
            85

<210> SEQ ID NO 4
<211> LENGTH: 136
<212> TYPE: PRT
<213> ORGANISM: Streptococcus mutans
<220> FEATURE:
<221> NAME/KEY: misc_feature
<223> OTHER INFORMATION: Amino acid sequence of the alpha-glucan binding
      domain from Streptococcus mutans

<400> SEQUENCE: 4

Met Gly Ser Thr Asn Gln Tyr Tyr Gln Leu Ala Asp Gly Lys Tyr Met
1               5                   10                  15
```

```
Leu Leu Asp Asp Ser Gly Arg Ala Lys Thr Gly Phe Val Leu Gln Asp
             20                  25                  30

Gly Val Leu Arg Tyr Phe Asp Gln Asn Gly Glu Gln Val Lys Asp Ala
         35                  40                  45

Ile Ile Val Asp Pro Asp Thr Asn Leu Ser Tyr Tyr Phe Asn Ala Thr
 50                  55                  60

Gln Gly Val Ala Val Lys Asn Asp Tyr Phe Glu Tyr Gln Gly Asn Trp
 65                  70                  75                  80

Tyr Leu Thr Asp Ala Asn Tyr Gln Leu Ile Lys Gly Phe Lys Ala Val
                 85                  90                  95

Asp Asp Ser Leu Gln His Phe Asp Glu Val Thr Gly Val Gln Thr Lys
            100                 105                 110

Asp Ser Ala Leu Ile Ser Ala Gln Gly Lys Val Tyr Gln Phe Asp Asn
        115                 120                 125

Asn Gly Asn Ala Val Ser Ala Arg
        130                 135

<210> SEQ ID NO 5
<211> LENGTH: 1250
<212> TYPE: DNA
<213> ORGANISM: Artificial Sequence
<220> FEATURE:
<223> OTHER INFORMATION: Synthetic: GBD-SSTad-SSTad
<220> FEATURE:
<221> NAME/KEY: CDS
<222> LOCATION: (115)..(1164)

<400> SEQUENCE: 5
ctcgagaaat cataaaaaat ttatttgctt tgtgagcgga taacaattat aatagattca      60
attgtgagcg gataacaatt tcacacagaa ttcattaaag aggagaaatt aact atg      117
                                                              Met
                                                              1 ggc tcc acc aat caa tat tat caa ctt gcc gat ggc aaa tat atg ctt      165
Gly Ser Thr Asn Gln Tyr Tyr Gln Leu Ala Asp Gly Lys Tyr Met Leu
         5                  10                  15 ctt gat gat tcc ggc agg gcc aaa acc ggc ttt gtt ctt caa gat ggc      213
Leu Asp Asp Ser Gly Arg Ala Lys Thr Gly Phe Val Leu Gln Asp Gly
             20                  25                  30 gtt ctt agg tat ttt gat caa aat ggc gaa caa gtt aaa gat gcc att      261
Val Leu Arg Tyr Phe Asp Gln Asn Gly Glu Gln Val Lys Asp Ala Ile
         35                  40                  45 att gtt gat ccc gat acc aat ctt tcc tat tat ttt aat gcc acc caa      309
Ile Val Asp Pro Asp Thr Asn Leu Ser Tyr Tyr Phe Asn Ala Thr Gln
 50                  55                  60                  65 ggc gtt gcc gtt aaa aat gat tat ttt gaa tat caa ggc aat tgg tat      357
Gly Val Ala Val Lys Asn Asp Tyr Phe Glu Tyr Gln Gly Asn Trp Tyr
                 70                  75                  80 ctt acc gat gcc aat tat caa ctt att aaa ggc ttt aaa gcc gtt gat      405
Leu Thr Asp Ala Asn Tyr Gln Leu Ile Lys Gly Phe Lys Ala Val Asp
             85                  90                  95 gat tcc ctt caa cat ttt gat gaa gtt acc ggc gtt caa acc aaa gat      453
Asp Ser Leu Gln His Phe Asp Glu Val Thr Gly Val Gln Thr Lys Asp
        100                 105                 110 tcc gcc ctt att tcc gcc caa ggc aaa gtt tat caa ttt gat aat aat      501
Ser Ala Leu Ile Ser Ala Gln Gly Lys Val Tyr Gln Phe Asp Asn Asn
    115                 120                 125 ggc aat gcc gtt tcc gcc agg tcc ggc ggc ggc tcc ggc ggc ggc           549
Gly Asn Ala Val Ser Ala Arg Ser Gly Gly Gly Ser Gly Gly Gly
130                 135                 140                 145
```

```
ggc tcc ggc ggc ggc tcc gcc ggc ggc ggc tcc agg tcc ggc        597
Gly Ser Gly Gly Gly Ser Ala Gly Gly Gly Ser Arg Ser Gly
            150                 155                 160 acc ggc tcc ggc gaa att gcc gcc ctt gaa caa gaa att gcc gcc ctt    645
Thr Gly Ser Gly Glu Ile Ala Ala Leu Glu Gln Glu Ile Ala Ala Leu
        165                 170                 175 gaa aaa gaa aat gcc gcc ctt gaa tgg gaa att gcc gcc ctt gaa caa    693
Glu Lys Glu Asn Ala Ala Leu Glu Trp Glu Ile Ala Ala Leu Glu Gln
    180                 185                 190 ggc ggc ccc ggc acc ggc aaa aat ttt ttt tgg aaa acc ttt acc tcc    741
Gly Gly Pro Gly Thr Gly Lys Asn Phe Phe Trp Lys Thr Phe Thr Ser
195                 200                 205 ggc acc ggc acc ggc tcc ggc gcc aaa att gcc gcc ctt aaa caa aaa    789
Gly Thr Gly Thr Gly Ser Gly Ala Lys Ile Ala Ala Leu Lys Gln Lys
210                 215                 220                 225 att gcc gcc ctt aaa tat aaa aat gcc gcc ctt aaa aaa aaa att gcc    837
Ile Ala Ala Leu Lys Tyr Lys Asn Ala Ala Leu Lys Lys Lys Ile Ala
                230                 235                 240 gcc ctt aaa caa ggc ggc ggc acc ggc tcc ggc acc agg tcc ggc acc    885
Ala Leu Lys Gln Gly Gly Gly Thr Gly Ser Gly Thr Arg Ser Gly Thr
            245                 250                 255 ggc tcc ggc gaa att gcc gcc ctt gaa caa gaa att gcc gcc ctt gaa    933
Gly Ser Gly Glu Ile Ala Ala Leu Glu Gln Glu Ile Ala Ala Leu Glu
        260                 265                 270 aaa gaa aat gcc gcc ctt gaa tgg gaa att gcc gcc ctt gaa caa ggc    981
Lys Glu Asn Ala Ala Leu Glu Trp Glu Ile Ala Ala Leu Glu Gln Gly
    275                 280                 285 ggc ccc ggc acc ggc aaa aat ttt ttt tgg aaa acc ttt acc tcc ggc   1029
Gly Pro Gly Thr Gly Lys Asn Phe Phe Trp Lys Thr Phe Thr Ser Gly
290                 295                 300                 305 acc ggc acc ggc tcc ggc gcc aaa att gcc gcc ctt aaa caa aaa att   1077
Thr Gly Thr Gly Ser Gly Ala Lys Ile Ala Ala Leu Lys Gln Lys Ile
            310                 315                 320 gcc gcc ctt aaa tat aaa aat gcc gcc ctt aaa aaa aaa att gcc gcc   1125
Ala Ala Leu Lys Tyr Lys Asn Ala Ala Leu Lys Lys Lys Ile Ala Ala
        325                 330                 335 ctt aaa caa ggc ggc ggc acc ggc tcc ggc acc agg tcc taaccggact    1174
Leu Lys Gln Gly Gly Gly Thr Gly Ser Gly Thr Arg Ser
    340                 345                 350 tcgaagcgtt cggttgggtc cggaatttcg tatggcaatg aaagacggtg agctggtgat   1234
atgggatagt gttcac                                                   1250

<210> SEQ ID NO 6
<211> LENGTH: 350
<212> TYPE: PRT
<213> ORGANISM: Artificial Sequence
<220> FEATURE:
<223> OTHER INFORMATION: Synthetic Construct

<400> SEQUENCE: 6

Met Gly Ser Thr Asn Gln Tyr Tyr Gln Leu Ala Asp Gly Lys Tyr Met
1               5                   10                  15

Leu Leu Asp Asp Ser Gly Arg Ala Lys Thr Gly Phe Val Leu Gln Asp
            20                  25                  30

Gly Val Leu Arg Tyr Phe Asp Gln Asn Gly Glu Gln Val Lys Asp Ala
        35                  40                  45

Ile Ile Val Asp Pro Asp Thr Asn Leu Ser Tyr Tyr Phe Asn Ala Thr
    50                  55                  60
```

```
Gln Gly Val Ala Val Lys Asn Asp Tyr Phe Tyr Gln Gly Asn Trp
 65                  70                  75                  80

Tyr Leu Thr Asp Ala Asn Tyr Gln Leu Ile Lys Gly Phe Lys Ala Val
                 85                  90                  95

Asp Asp Ser Leu Gln His Phe Asp Glu Val Thr Gly Val Gln Thr Lys
            100                 105                 110

Asp Ser Ala Leu Ile Ser Ala Gln Gly Lys Val Tyr Gln Phe Asp Asn
        115                 120                 125

Asn Gly Asn Ala Val Ser Ala Arg Ser Gly Gly Gly Ser Gly Gly
    130                 135                 140

Gly Gly Ser Gly Gly Gly Gly Ser Ala Gly Gly Gly Ser Arg Ser
145                 150                 155                 160

Gly Thr Gly Ser Gly Glu Ile Ala Ala Leu Glu Gln Glu Ile Ala Ala
                165                 170                 175

Leu Glu Lys Glu Asn Ala Ala Leu Glu Trp Glu Ile Ala Ala Leu Glu
            180                 185                 190

Gln Gly Gly Pro Gly Thr Gly Lys Asn Phe Phe Trp Lys Thr Phe Thr
        195                 200                 205

Ser Gly Thr Gly Thr Gly Ser Gly Ala Lys Ile Ala Ala Leu Lys Gln
210                 215                 220

Lys Ile Ala Ala Leu Lys Tyr Lys Asn Ala Ala Leu Lys Lys Lys Ile
225                 230                 235                 240

Ala Ala Leu Lys Gln Gly Gly Thr Gly Ser Gly Thr Arg Ser Gly
                245                 250                 255

Thr Gly Ser Gly Glu Ile Ala Ala Leu Glu Gln Glu Ile Ala Ala Leu
            260                 265                 270

Glu Lys Glu Asn Ala Ala Leu Glu Trp Glu Ile Ala Ala Leu Glu Gln
        275                 280                 285

Gly Gly Pro Gly Thr Gly Lys Asn Phe Phe Trp Lys Thr Phe Thr Ser
    290                 295                 300

Gly Thr Gly Thr Gly Ser Gly Ala Lys Ile Ala Ala Leu Lys Gln Lys
305                 310                 315                 320

Ile Ala Ala Leu Lys Tyr Lys Asn Ala Ala Leu Lys Lys Lys Ile Ala
                325                 330                 335

Ala Leu Lys Gln Gly Gly Gly Thr Gly Ser Gly Thr Arg Ser
            340                 345                 350

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Asn Phe Phe Trp Lys Thr Phe Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Phe Phe Trp Lys Thr Phe
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Phe Trp Lys Thr
1

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Pro Gly Ser Gly Ser Gly Ser Gly Ser Gly Ser Ala
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Ala Gly Cys Lys Asn Phe Phe Trp Lys Thr Phe Thr Ser Cys
1               5                   10
```

We claim:

1. A recombinant GBD-SSTad-SSTad protein having a molecular weight of 39.5 kDa, comprising 2 fragments of the SST protein having the sequence SEQ ID NO 1, a spacer having the sequence SEQ ID NO 2 and a spacer having the sequence SEQ ID NO 3, alpha-glucan binding domain from *Streptococcus mutans* having the sequence SEQ ID NO 4, which protein is encoded by the nucleotide sequence of the GBD-SSTad-SSTad gene SEQ ID NO 5.

2. A method for preparation of recombinant GBD-SSTad-SSTad protein according to claim 1 on glucan, which method comprises: binding of GBD-SSTad-SSTad protein in cell extracts of *E. coli* BL21 [pGBD-SSTad-SSTad] strain to an alpha-glycan-containing sorbent due to affinity interaction during the incubation procedure, subsequent washing from unbound bacterial proteins and isolation of the desired product.

3. A pharmaceutical composition in the form of an injectable preparation for enhancing folliculogenesis and spermatogenesis in mammals, birds and humans, which composition comprises recombinant GBD-SSTad-SSTad protein according to claim 1 and an adjuvant suitable for injection.

4. The pharmaceutical composition according to claim 3, wherein said composition is comprised in one or more containers enclosed in a package with leaflet containing directions for use.

5. The pharmaceutical composition according to claim 3, wherein the pharmaceutical composition is a vaccine.

6. A method of increasing folliculogenesis and spermatogenesis in mammals, birds and humans, which method comprises administering subcutaneous or intramuscular injections of a preparation comprising recombinant GBD-SSTad-SSTad protein according to claim 1, at a dose of 5-50 µg of said protein per kilogram of body weight of a mammal or bird.

* * * * *